United States Patent
Neftel et al.

(10) Patent No.: US 8,585,634 B2
(45) Date of Patent: Nov. 19, 2013

(54) SYSTEM FOR PERFORMING PERITONEAL DIALYSIS

(75) Inventors: Frédéric Neftel, Lausanne (CH); Florent Junod, Nyon (CH); Didier Vecten, Lausanne (CH)

(73) Assignee: Debiotech S.A., Lausanne (CH)

( * ) Notice: Subject to any disclaimer, the term of this patent is extended or adjusted under 35 U.S.C. 154(b) by 1548 days.

(21) Appl. No.: 10/565,810

(22) PCT Filed: Aug. 2, 2004

(86) PCT No.: PCT/CH2004/000480
§ 371 (c)(1),
(2), (4) Date: Feb. 9, 2006

(87) PCT Pub. No.: WO2005/009511
PCT Pub. Date: Feb. 3, 2005

(65) Prior Publication Data
US 2008/0058711 A1 Mar. 6, 2008

(30) Foreign Application Priority Data

Jul. 31, 2003 (WO) ...................... PCT/CH03/00527
Jan. 26, 2004 (WO) .................. PCT/CH2004/00040

(51) Int. Cl.
*A61M 1/00* (2006.01)
(52) U.S. Cl.
USPC ............. 604/29; 604/131; 604/151; 604/153; 137/597; 417/477.2; 417/477.3
(58) Field of Classification Search
USPC .................. 604/29, 131, 890.1, 151, 153; 417/477.2, 477.3; 251/89, 93, 287, 251/355, 335.1, 335.2, 358; 137/561 A, 137/561 R, 270, 597
See application file for complete search history.

(56) References Cited

U.S. PATENT DOCUMENTS

| 2,684,829 A | * | 7/1954 | McFarland, Jr. | ............... 251/331 |
| 4,530,647 A | * | 7/1985 | Uno | ........................... 417/477.3 |

(Continued)

FOREIGN PATENT DOCUMENTS

| DE | 198 14 695 | 10/1999 |
| DE | 198 56 744 | 6/2000 |

(Continued)

OTHER PUBLICATIONS

International Search Report.

(Continued)

*Primary Examiner* — Bhisma Mehta
*Assistant Examiner* — Larry R Wilson
(74) *Attorney, Agent, or Firm* — Nixon & Vanderhye P.C.

(57) ABSTRACT

The invention concerns a system and a method of use of said system for performing fluid administration on a patient, the system comprising a liquid pump, a liquid distribution system, a liquid supply means, and patient conduit. The liquid distribution system comprises two distinct hub chambers. The first hub chamber includes at least one liquid supply port with a dedicated valve means, one patient port with dedicated valve means, and one pump inlet. The second hub chamber includes at least one patient port or warmer port with dedicated valve means and one pump outlet. The system further comprises control means arranged to close the patient port of the first hub chamber when the liquid supply port is open, and vice versa.

64 Claims, 41 Drawing Sheets

(56) References Cited

U.S. PATENT DOCUMENTS

| | | | | |
|---|---|---|---|---|
| 4,586,920 A | * | 5/1986 | Peabody | 604/29 |
| 4,758,228 A | * | 7/1988 | Williams | 604/153 |
| 4,828,545 A | * | 5/1989 | Epstein et al. | 604/66 |
| 4,952,372 A | * | 8/1990 | Huber | 422/81 |
| 4,980,054 A | | 12/1990 | Lavender | |
| 5,078,362 A | | 1/1992 | Lawless et al. | |
| 5,350,357 A | * | 9/1994 | Kamen et al. | 604/29 |
| 5,437,629 A | * | 8/1995 | Goldrath | 604/21 |
| 5,478,211 A | * | 12/1995 | Dominiak et al. | 417/234 |
| 5,518,378 A | * | 5/1996 | Neftel et al. | 417/477.2 |
| 5,641,405 A | * | 6/1997 | Keshaviah et al. | 210/645 |
| 5,683,233 A | * | 11/1997 | Moubayed et al. | 417/474 |
| 5,722,947 A | * | 3/1998 | Jeppsson et al. | 604/29 |
| 5,840,069 A | * | 11/1998 | Robinson | 604/131 |
| 6,074,359 A | | 6/2000 | Keshaviah et al. | |
| 6,296,450 B1 | * | 10/2001 | Westberg et al. | 417/18 |

FOREIGN PATENT DOCUMENTS

| | | |
|---|---|---|
| DE | 198 56 744 A1 | 6/2000 |
| DE | 101 24 951 | 12/2002 |
| DE | 101 24 951 C1 | 12/2002 |
| EP | 0 956 876 A1 | 11/1999 |
| EP | 1 195 171 | 4/2002 |
| EP | 1 195 171 A2 | 4/2002 |
| EP | 1195171 A2 * | 4/2002 |
| EP | 1 277 485 B1 | 11/2006 |
| WO | WO 99/06082 A1 | 2/1999 |
| WO | WO 00/30701 | 6/2000 |
| WO | WO 01/19430 A1 | 3/2001 |

OTHER PUBLICATIONS

Feb. 17, 2012 Opposition from Fresenius Medical Care Deutschland to Ep 1 648 536 — Opposition letter from Fresenius' agents w/documents cited therein.

U.S. Office Action in U.S. Appl. No. 10/565,782 dated May 15, 2007.

* cited by examiner

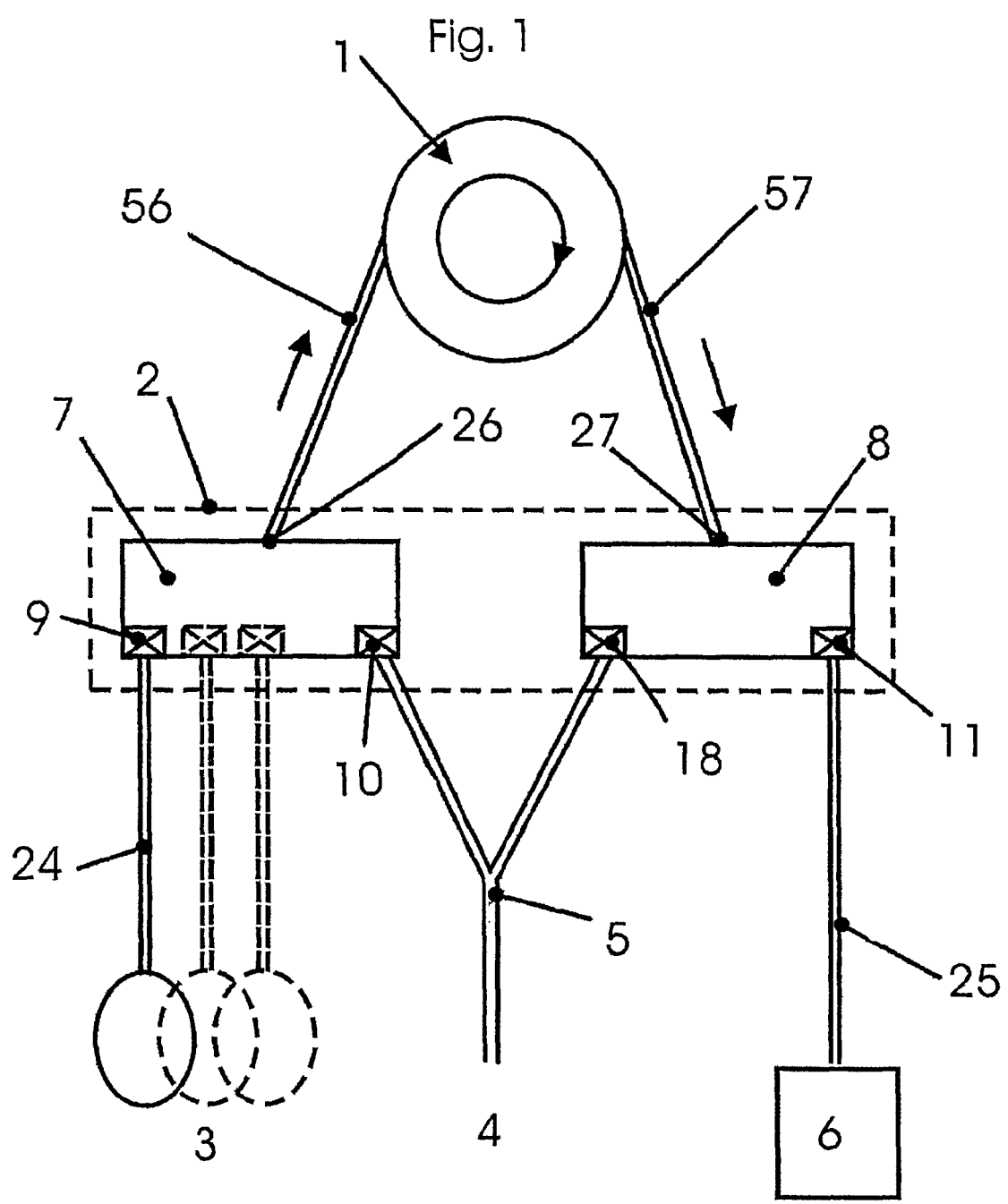

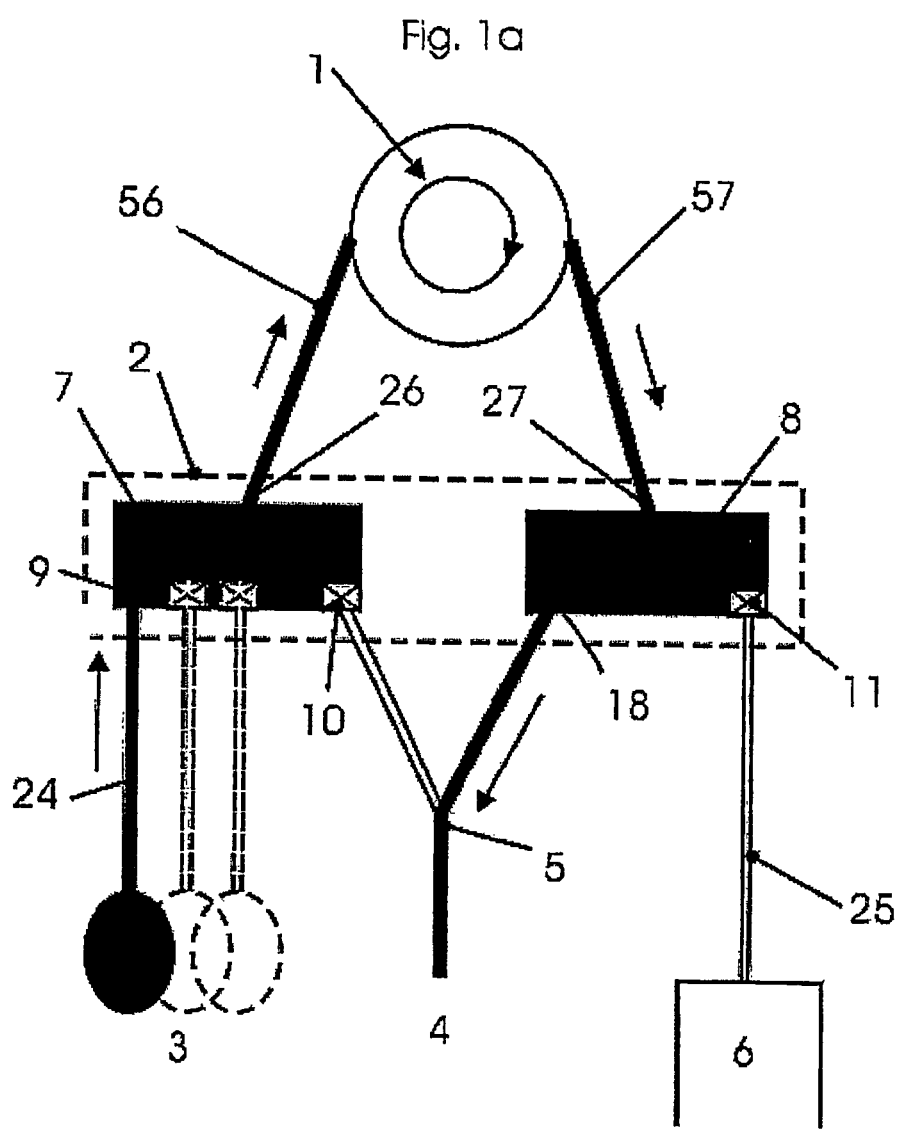

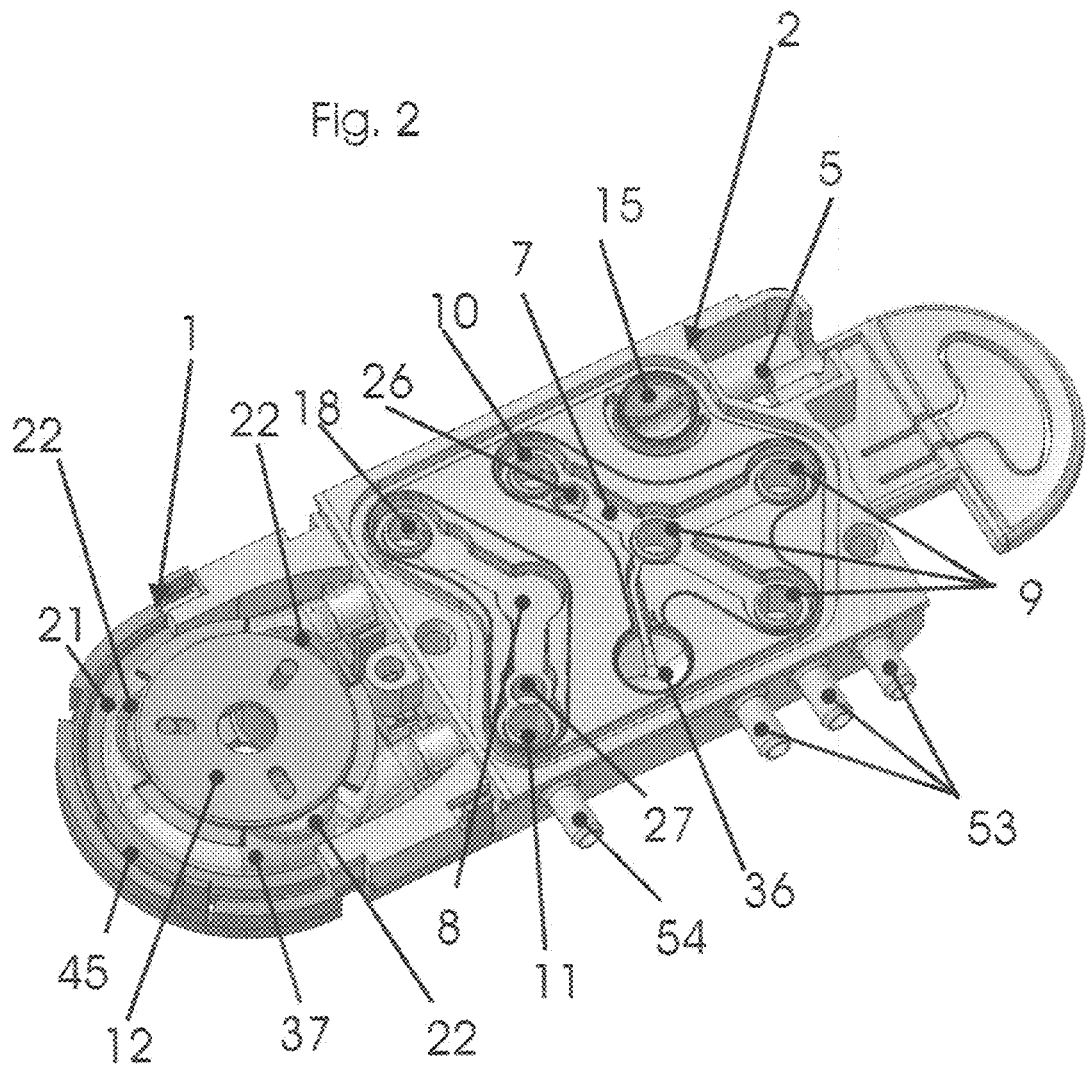

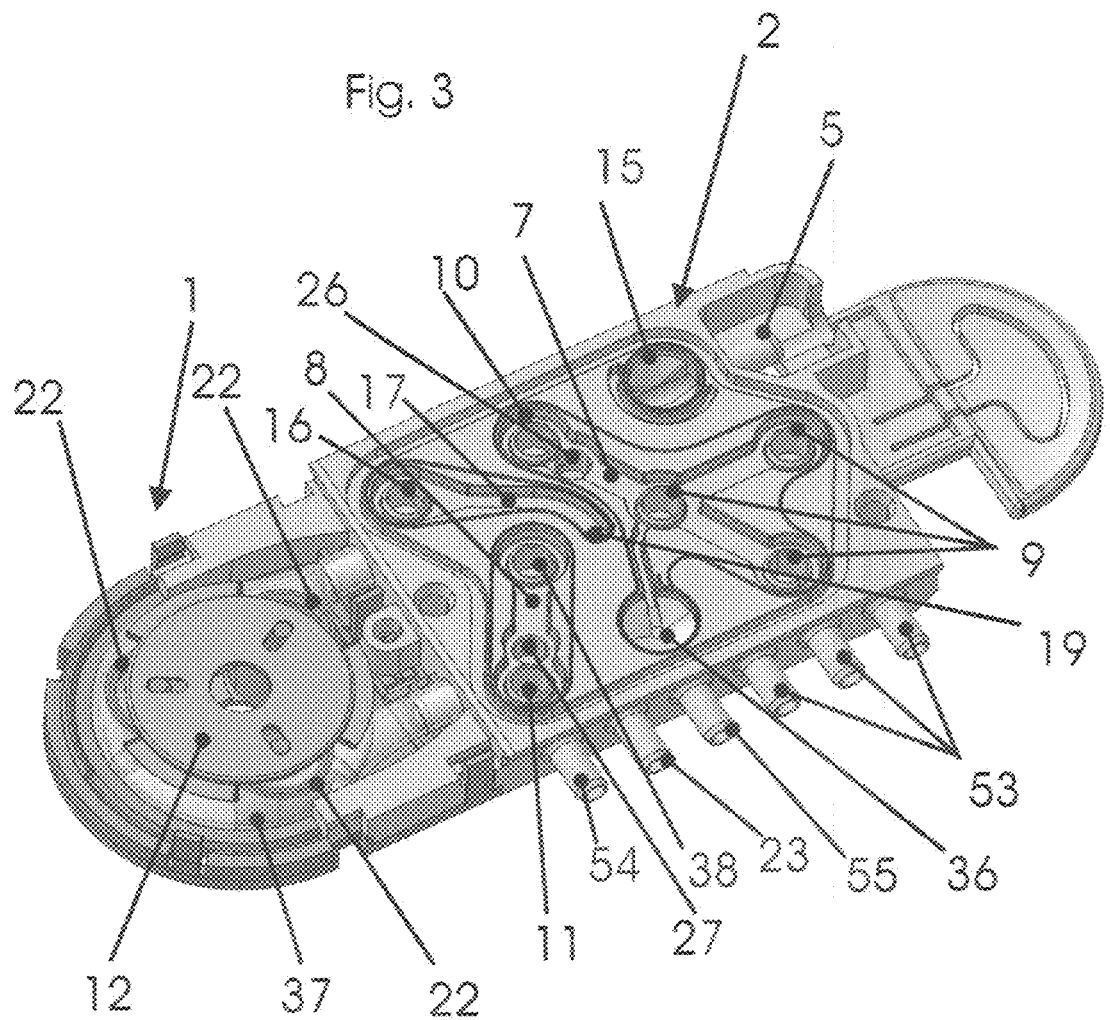

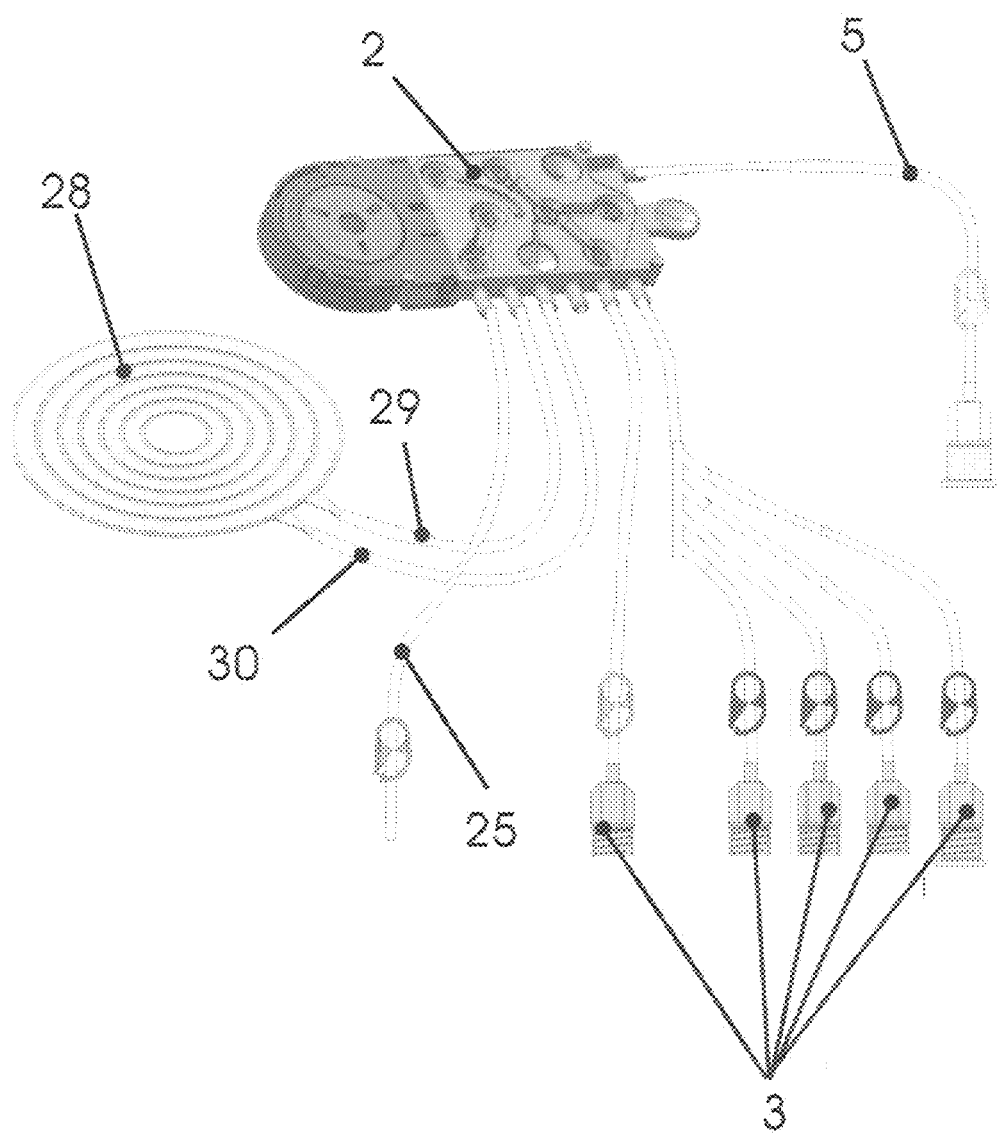

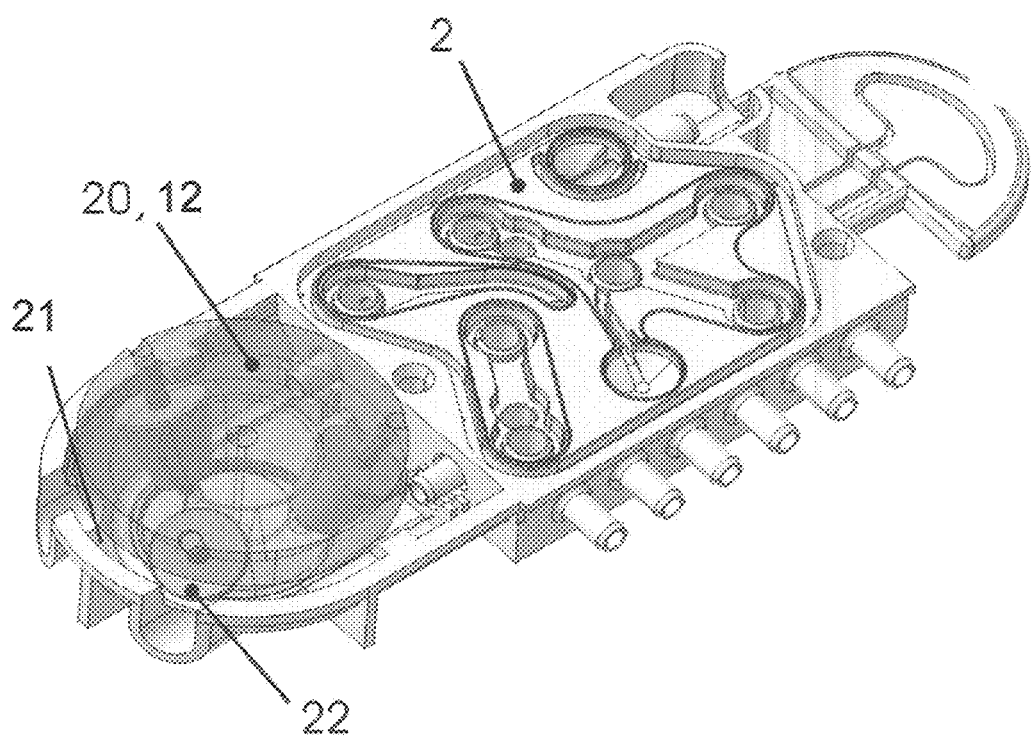

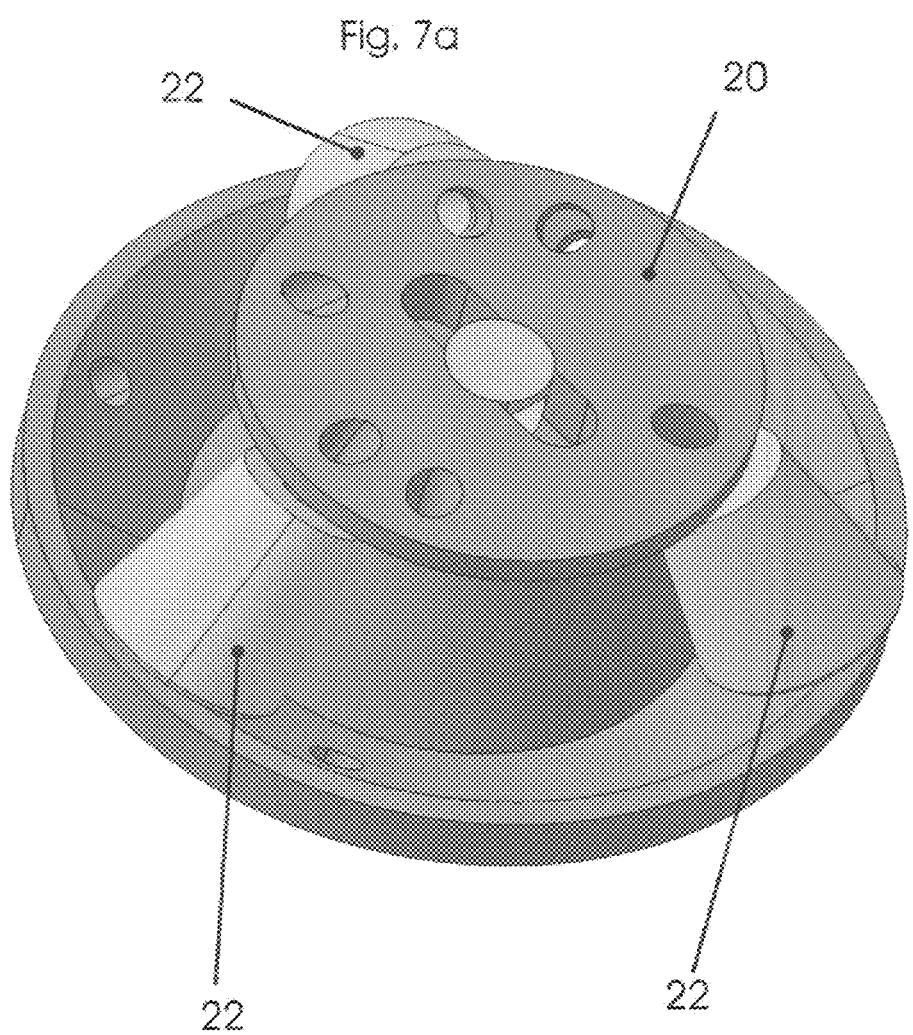

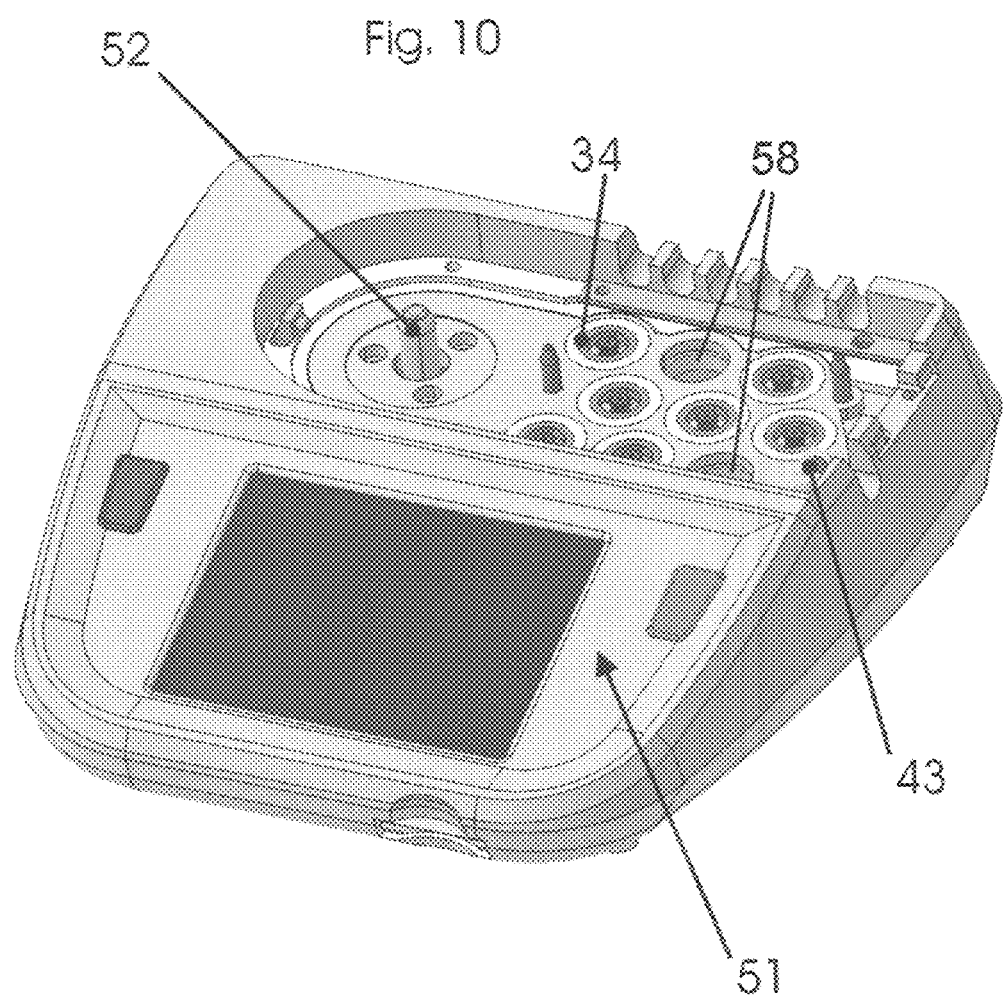

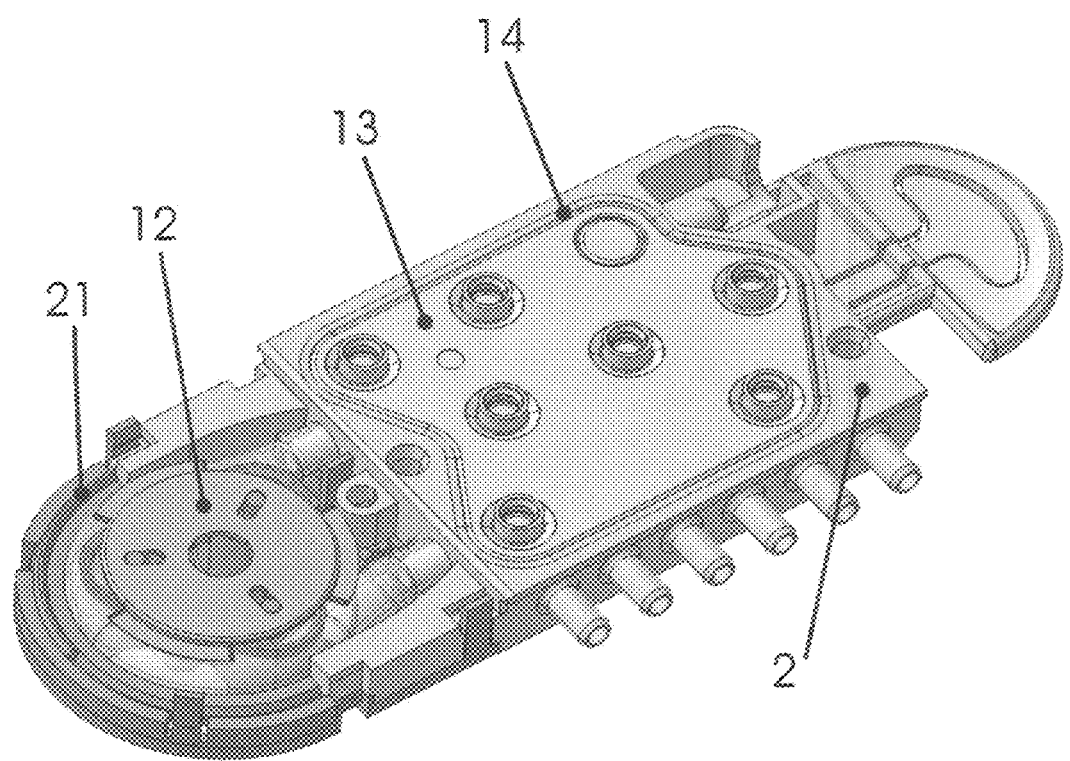

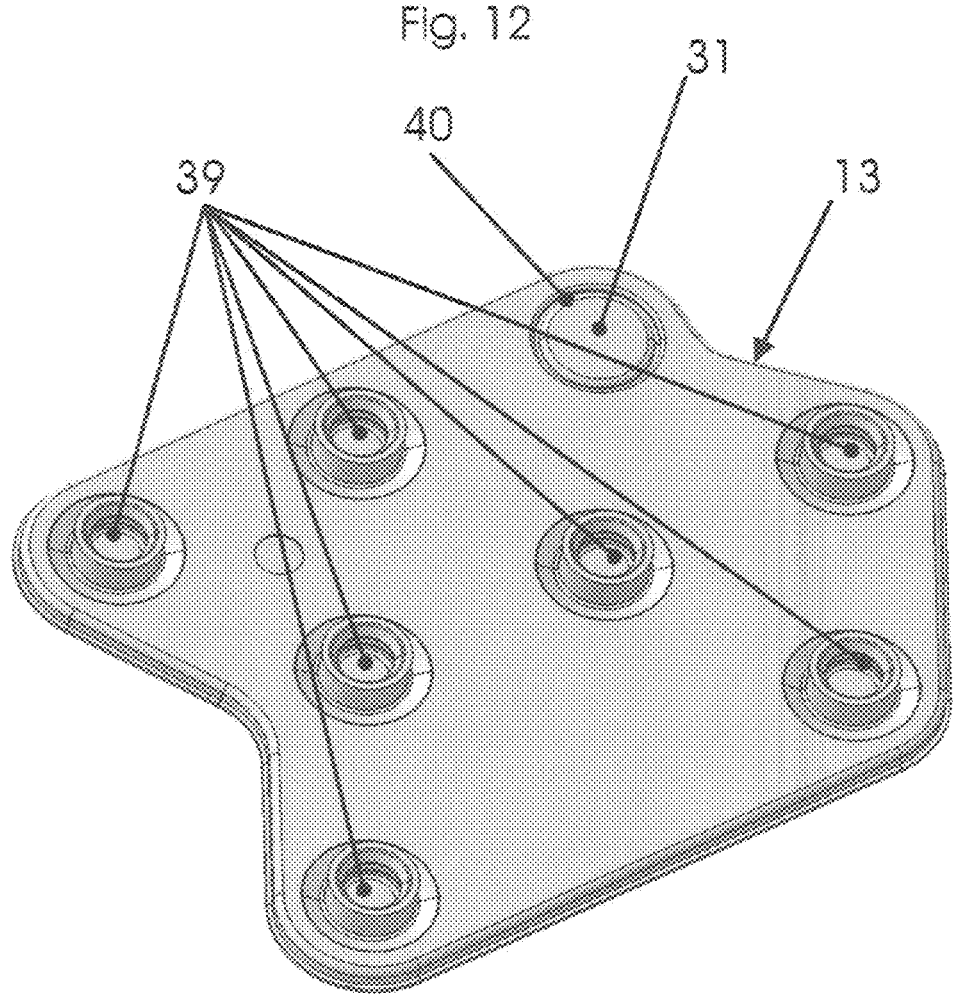

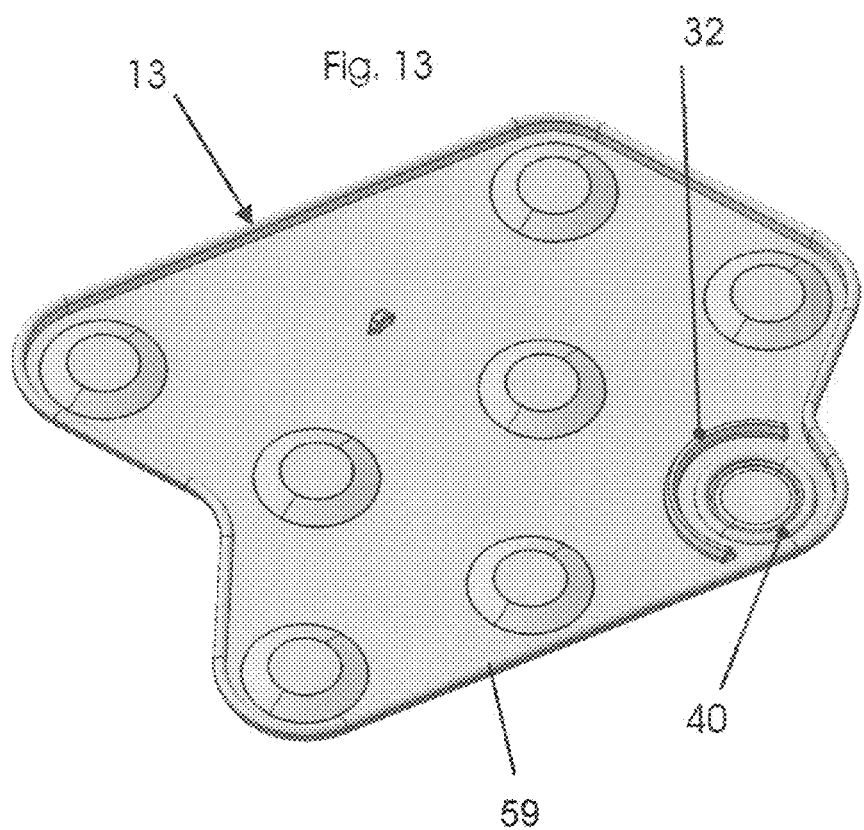

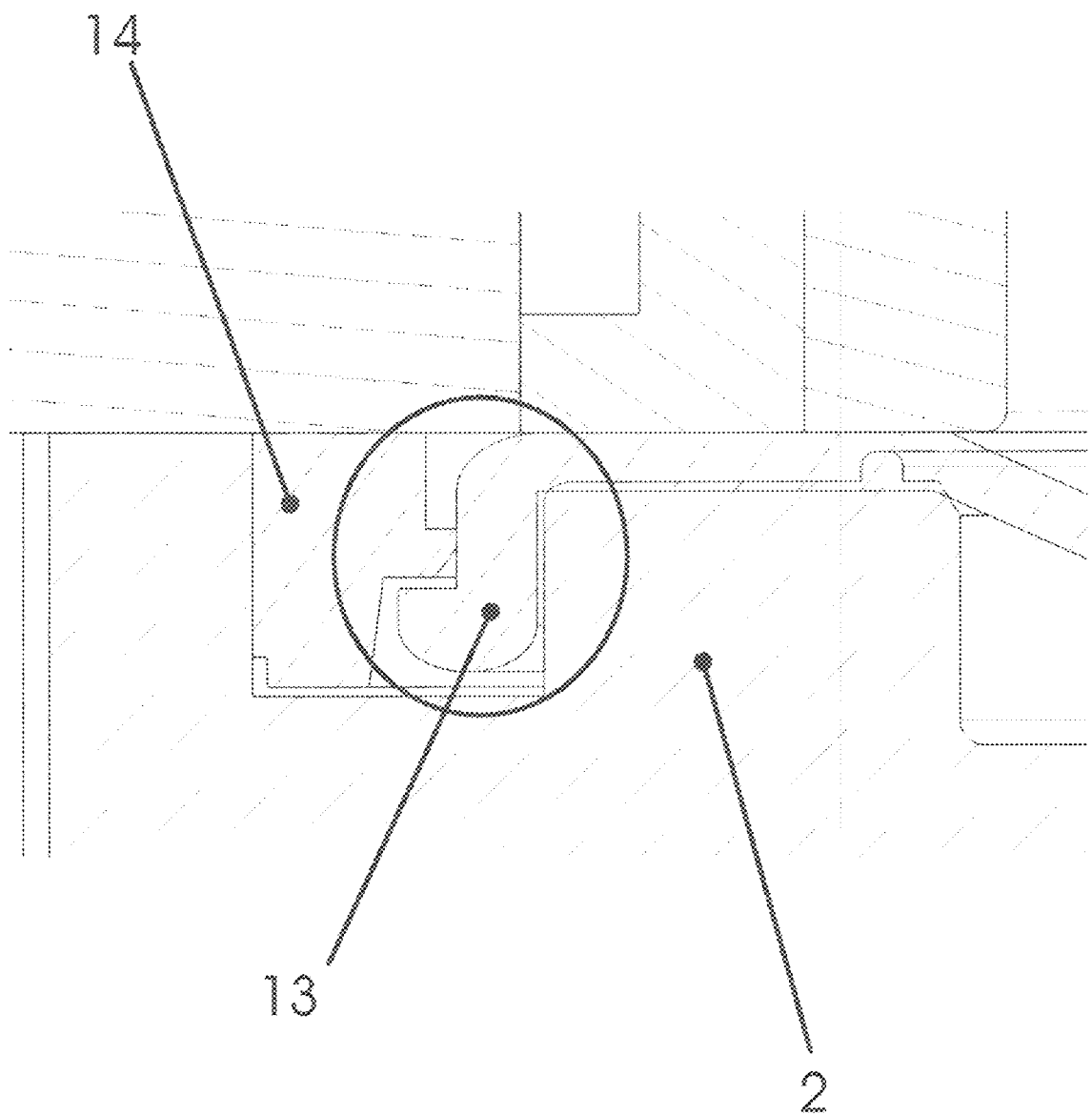

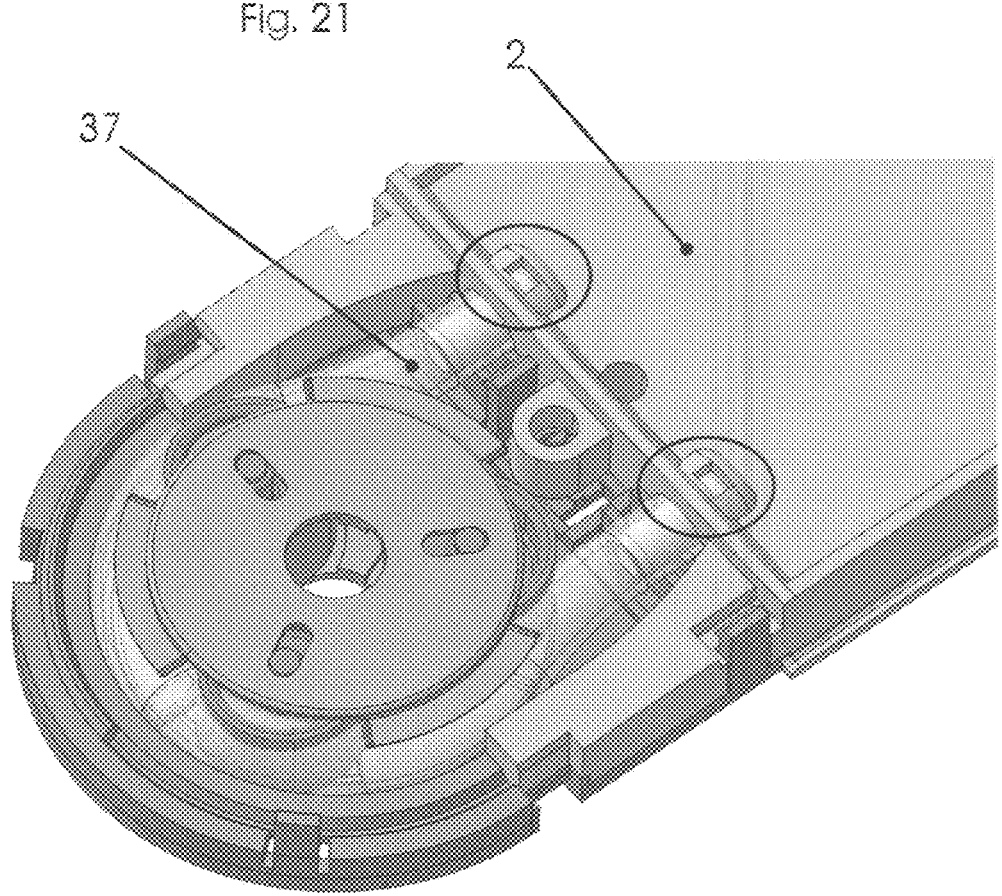

FIG. 25

DRAIN ANALISYS APD

| [min] | Cycle 1 Vol. [ml] | Cycle 1 Q [l/[min] | | Cycle 2 Vol. [ml] | Cycle 2 Q [l/[min] | | Cycle 3 Vol. [ml] | Cycle 3 Q [l/[min] | | Cycle 4 Vol. [ml] | Cycle 4 Q [l/[min] | | Cycle 5 Vol. [ml] | Cycle 5 Q [l/[min] |
|---|---|---|---|---|---|---|---|---|---|---|---|---|---|---|
| 0 | 2330 | | | 2752 | | | 2503 | | | 2665 | | | 2736 | |
| 1 | 2131 | 0.199 | | 2600 | 0.152 | | 2294 | 0.209 | | 2490 | 0.175 | | 2580 | 0.156 |
| 2 | 1900 | 0.231 | | 2375 | 0.225 | | 2087 | 0.207 | | 2253 | 0.237 | | 2348 | 0.232 |
| 3 | 1681 | 0.219 | | 2158 | 0.217 | | 1860 | 0.227 | | 2035 | 0.218 | | 2120 | 0.228 |
| 4 | 1453 | 0.228 | | 1941 | 0.217 | | 1637 | 0.223 | | 1809 | 0.226 | | 1892 | 0.228 |
| 5 | 1233 | 0.220 | | 1725 | 0.216 | | 1420 | 0.217 | | 1585 | 0.224 | | 1651 | 0.241 |
| 6 | 1023 | 0.210 | | 1499 | 0.226 | | 1193 | 0.227 | | 1369 | 0.216 | | 1421 | 0.230 |
| 7 | 797 | 0.226 | | 1292 | 0.207 | | 976 | 0.217 | | 1143 | 0.226 | | 1200 | 0.221 |
| 8 | 579 | 0.218 | | 1075 | 0.217 | | 750 | 0.226 | | 927 | 0.216 | | 991 | 0.209 |
| 9 | 367 | 0.212 | | 848 | 0.227 | | 532 | 0.218 | | 721 | 0.206 | | 784 | 0.207 |
| 10 | 173 | 0.194 | | 644 | 0.204 | | 326 | 0.206 | | 512 | 0.209 | | 583 | 0.201 |
| 11 | 72 | 0.101 | treshold 1 | 437 | 0.207 | | 147 | 0.179 | treshold 1 | 433 | 0.079 | | 404 | 0.179 |
| 12 | 50 | 0.022 | treshold 2 | 232 | 0.205 | | 72 | 0.075 | treshold 2 | 374 | 0.059 | treshold 1 | 302 | 0.102 |
| 13 | 29 | 0.021 | Q [l/[min] | 74 | 0.158 | treshold 1 | 35 | 0.037 | Q [l/[min] | 307 | 0.067 | treshold 2 | 228 | 0.074 |
| 14 | 20 | 0.009 | 0.216 | 59 | 0.035 | treshold 2 | 4 | 0.031 | 0.2142 | 213 | 0.094 | Q [l/[min] | 185 | 0.043 |
| 15 | 11 | 0.016 | 0.101 | 25 | 0.014 | Q [l/[min] | 0 | 0.004 | 0.075 | 169 | 0.044 | 0.2153 | 172 | 0.013 |
| 16 | | | 0.017 | 10 | 0.048 | 0.21 | | | 0.024 | 121 | 0.048 | | 135 | 0.038 |
| 17 | | | | 0 | 0.074 | 0.158 | | | | 79 | 0.042 | | 97 | 0.007 |
| 18 | | | | | | 0.0185 | | | | 46 | 0.035 | | 80 | 0.016 |
| 19 | | | | | | | | | | 25 | 0.020 | | 64 | 0.012 |
| 20 | | | | | | | | | | 5 | 0.021 | | 52 | 0.020 |
| 21 | | | | | | | | | | 0 | 0.005 | 0.075 | 18 | 0.025 |
| 22 | | | | | | | | | | | | 0.030 | 6 | 0.006 |
| 23 | | | | | | | | | | | | | 0 | 0.001 |
| 24 | | | | | | | | | | | | | | | treshold 1: 0.212
treshold 2: 0.088
Q [l/[min]: 0.021

Patient BH

SYSTEM FOR PERFORMING PERITONEAL DIALYSIS

This application is the US national phase of international application PCT/CH2004/000480 filed 2 Aug. 2004 which designated the U.S. and claims benefit of PCT/CH3/00527, dated 31 Jul. 2003 and PCT/CH04/000040, dated 26 Jan. 2004, the entire content of which is hereby incorporated by reference.

FIELD OF THE INVENTION

The present invention relates to systems for performing peritoneal dialysis on a patient and more precisely to such systems which include a liquid distribution system forming a distinct element.

STATE OF THE ART

Peritoneal dialysis systems as defined above are described in the following patent documents: EP 0 790 841 B1, EP 0 695 397 B1, EP 0 852 953 B1, EP 0 694 125 B1, EP 0 686 237 B1, EP 0 471 000 B1, EP 0 332 690 B1, EP 0 262 182 B1, EP 0 259 464 B1 and EP 1 195 171 A2.

SUMMARY OF THE INVENTION

An objective of the present invention is to provide an improved peritoneal dialysis system and in particular an improved liquid distribution system.

This objective and many others are achieved with the system as defined in claim 1 and 38.

Preferred embodiments of the invention are defined in dependent claims 2 to 37 and 40 to 46.

Several advantages result from the invention, in particular:
- simpler, and therefore more efficient, liquid distribution system which may include only two distinct cavities,
- possibility to use a peristaltic pump, in particular a rotatable peristaltic pump,
- possibility to use an unidirectional pump which results in a higher precision and a longer life time,
- possibility to fix the liquid distribution system and the pump together, alternatively with vibration attenuating means,
- possibility to use a flexible membrane which covers the chambers and which include valve elements,
- the membrane may be molded,
- part of a pressure sensor can be incorporated in the membrane.

Those and other advantages will be better understood in the detailed description of the invention exemplified here below, together with the following figures.

SHORT DESCRIPTION OF THE FIGURES

FIG. 1 shows in a schematic way the principle of the invention

FIG. 1A shows the "fill" phase

FIG. 2 illustrates a first embodiment of the invention (liquid distribution system)

FIG. 3 illustrates a second embodiment (disposable cartridge) including a warmer chamber

Figure 8:
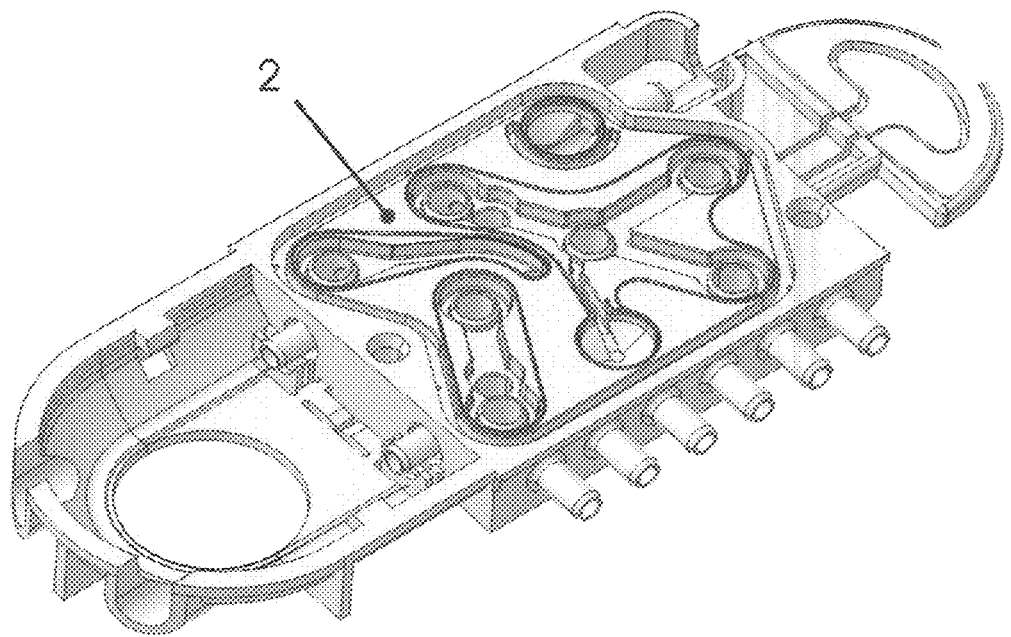
Figure 9:
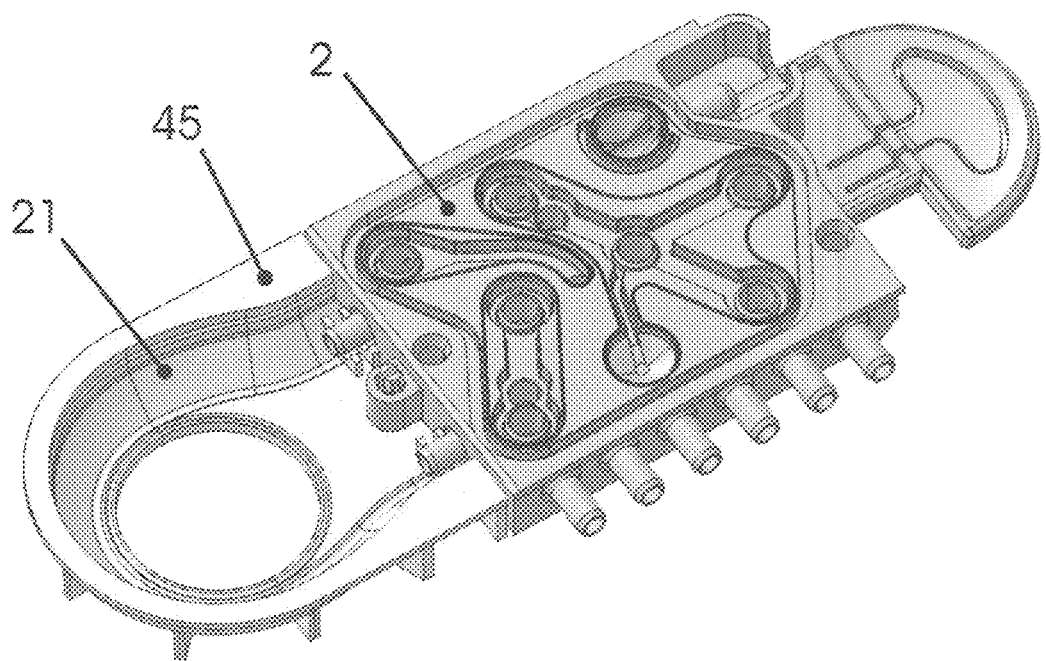

FIG. 6 illustrates the disposable cartridge of FIG. 3 with the complete tubing set FIG. 7 shows an embodiment with the rotative parts (rollers) integrated on the cycler FIG. 8 shows the embodiment of FIG. 7 without the rollers FIG. 9 the disposable cartridge in two parts allowing to absorb pump vibrations FIG. 10 shows a cycler without the cartridge insertion slot FIG. 11 illustrates a disposable cartridge opened showing the peritoneal pump FIG. 12 is an upper view of an elastic molded membrane FIG. 13 is a bottom view of the membrane of FIG. 12

FIG. 14 shows a membrane clipping system

Figure 15:
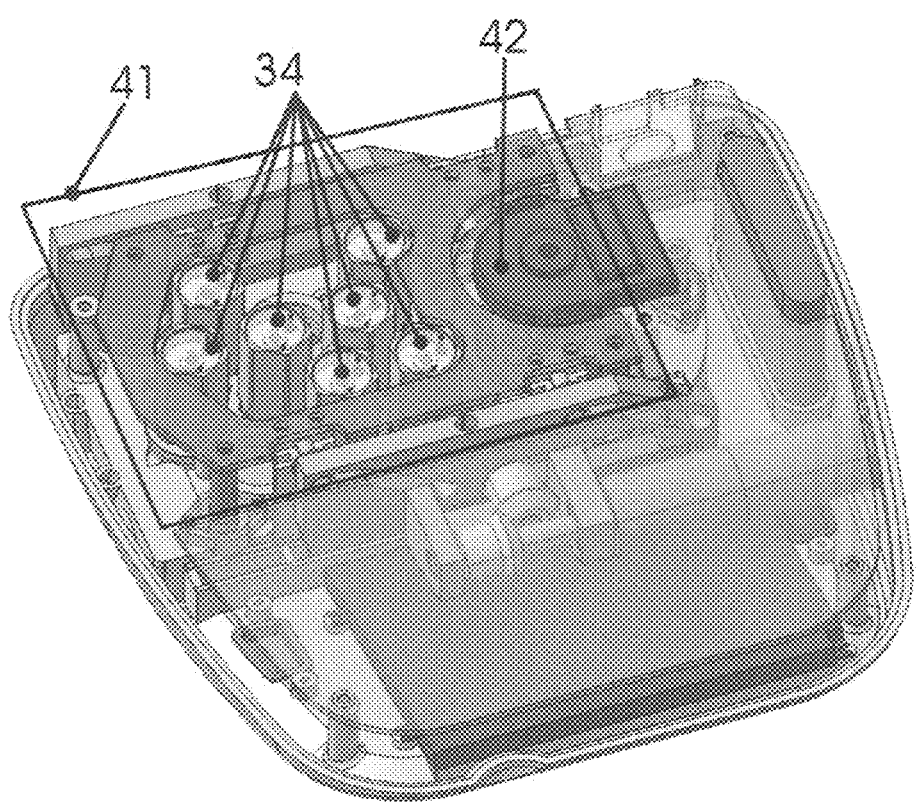

FIG. 15 shows the cycler of FIG. 10 in an open state

Figure 16:
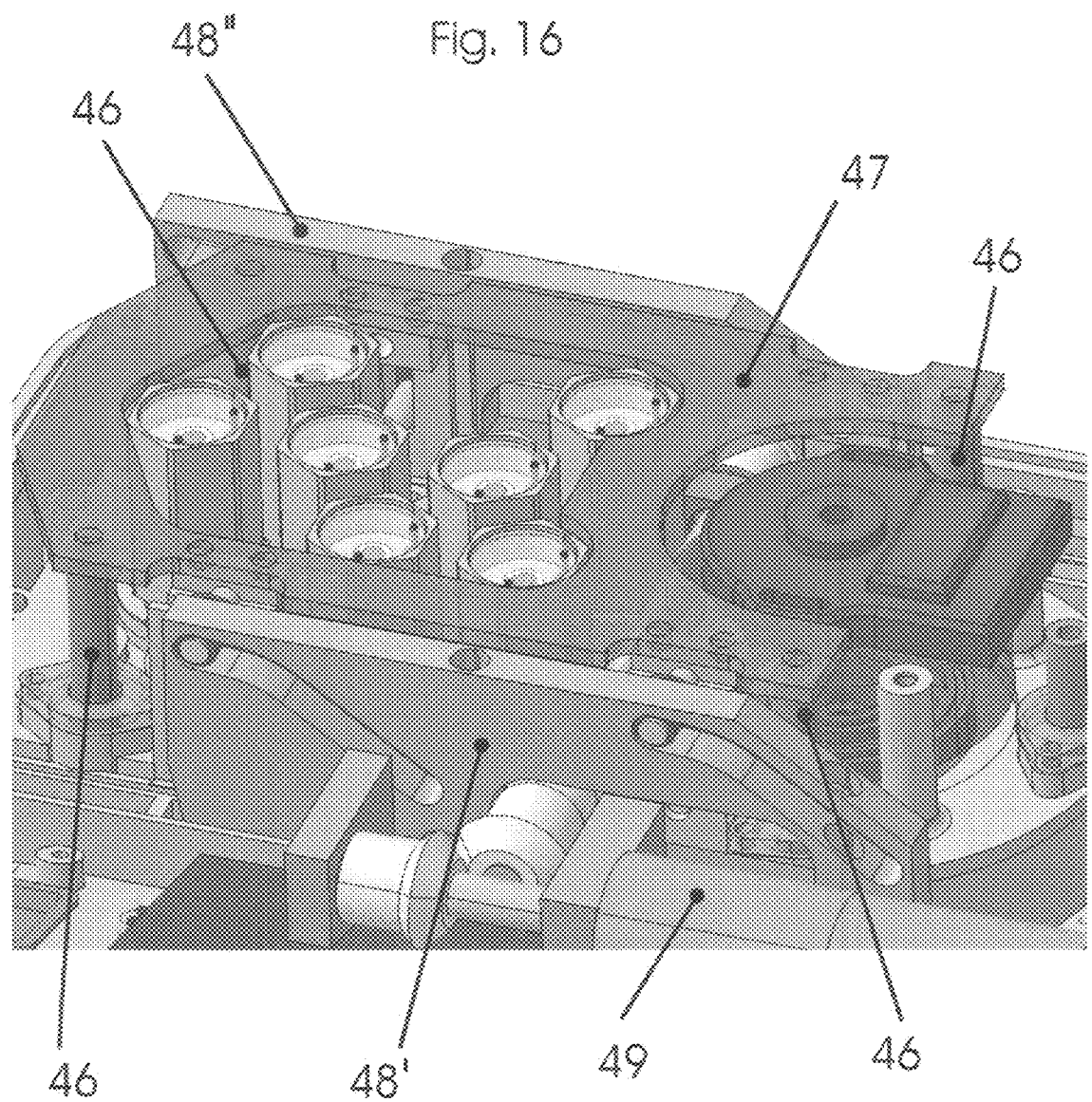

FIG. 16 shows a cartridge loader

Figure 17:
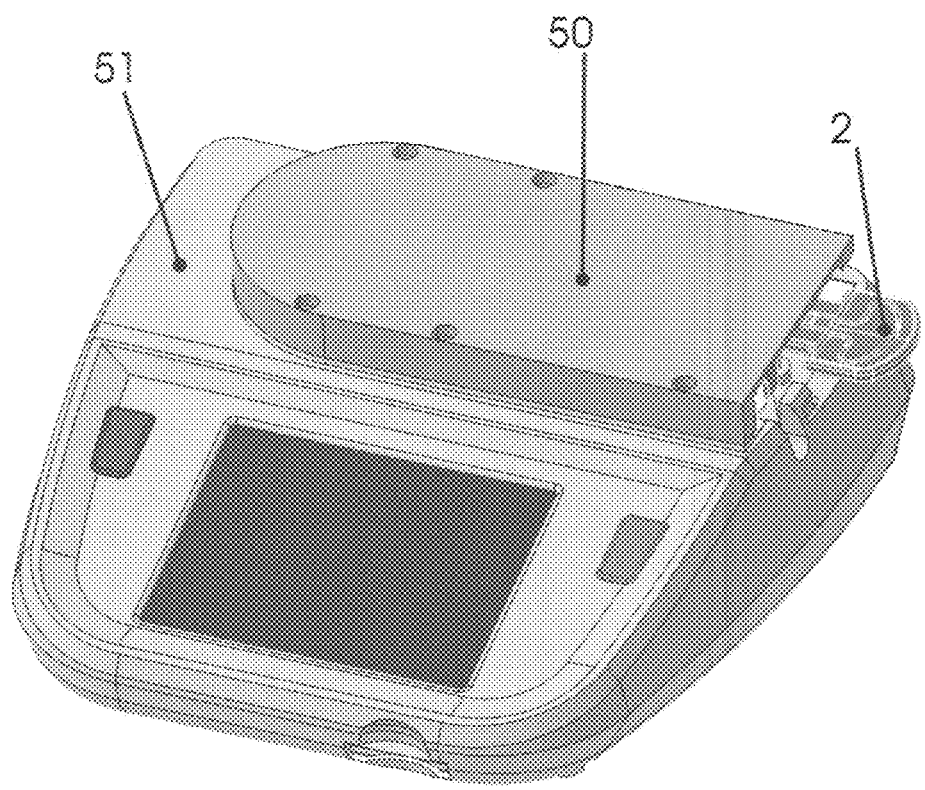
Figure 18:
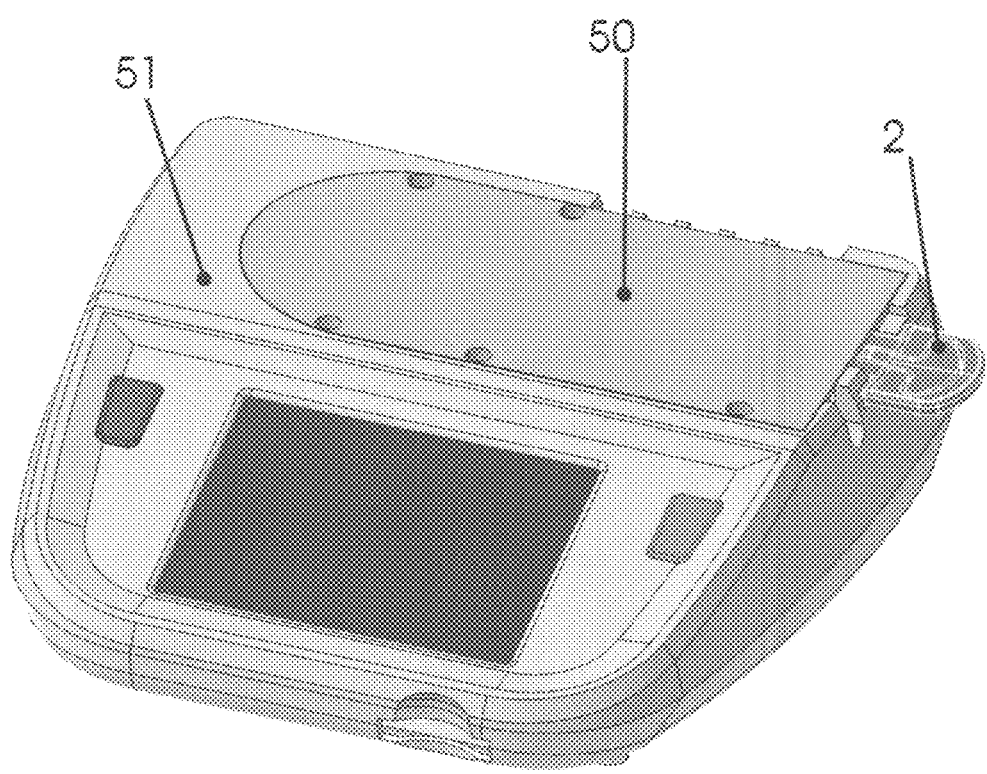
Figure 19:
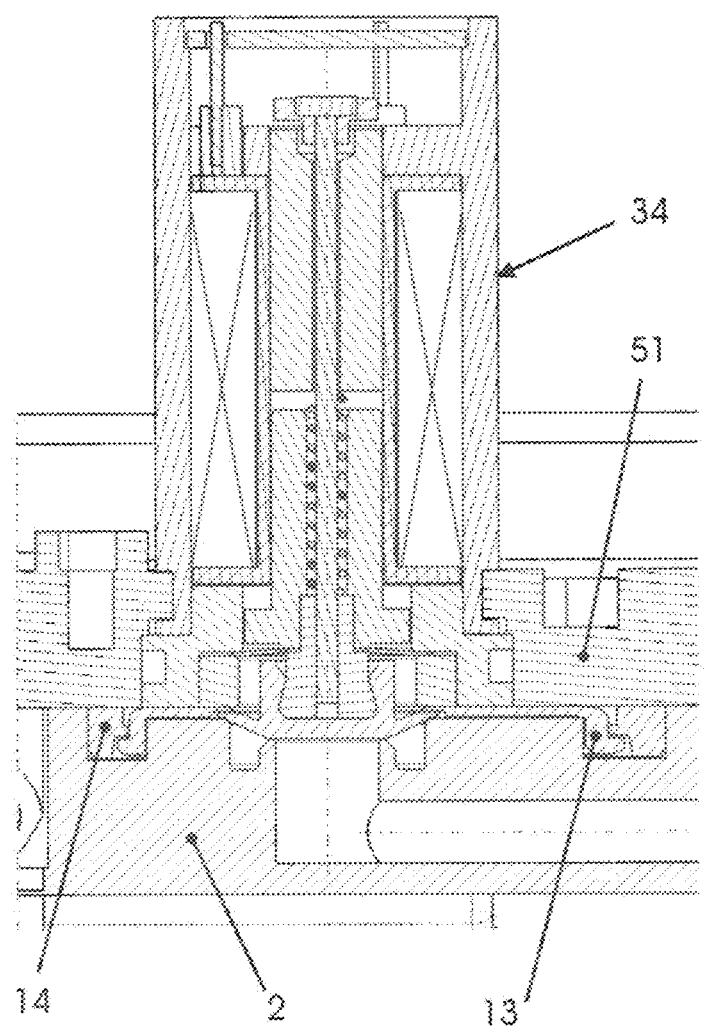
Figure 20:
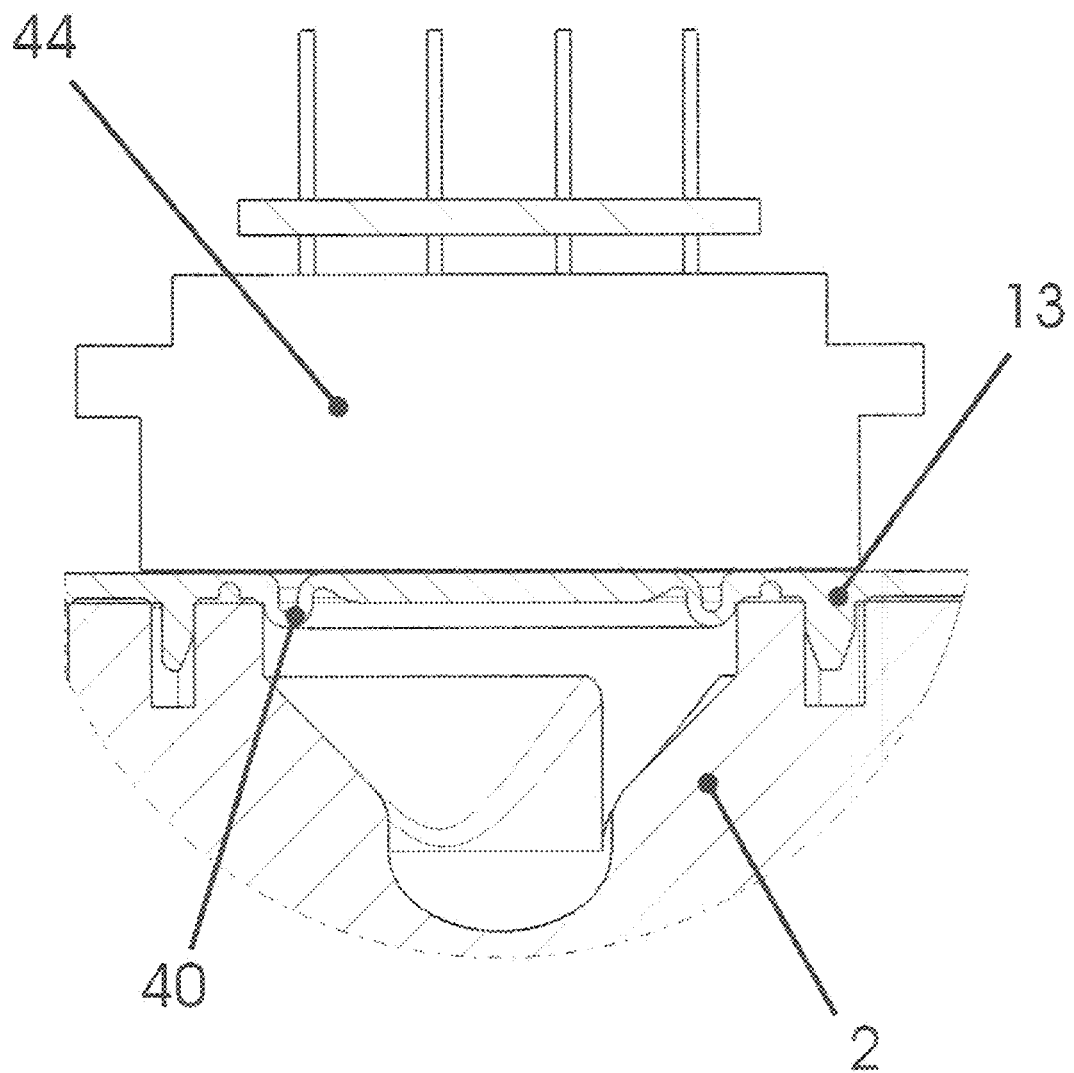
Figure 22A:
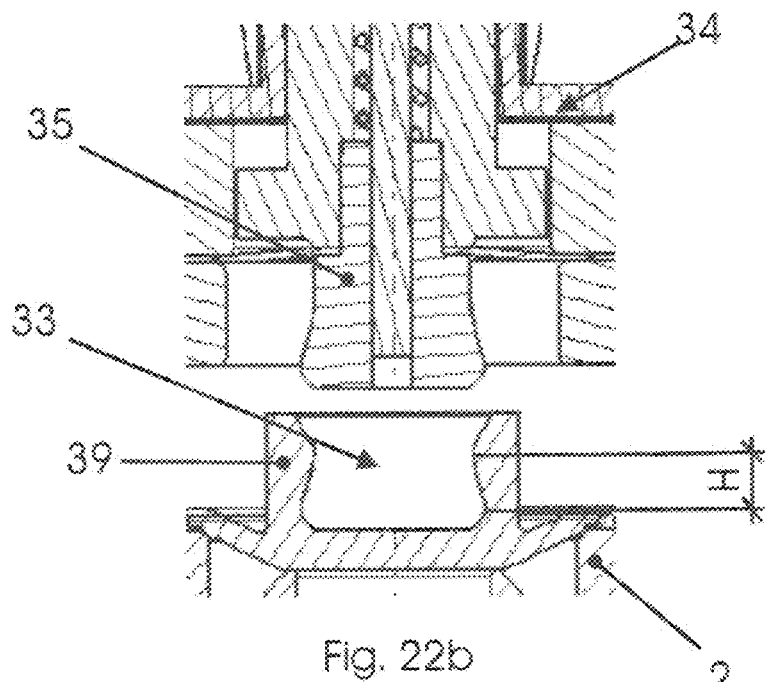
Figure 22B:
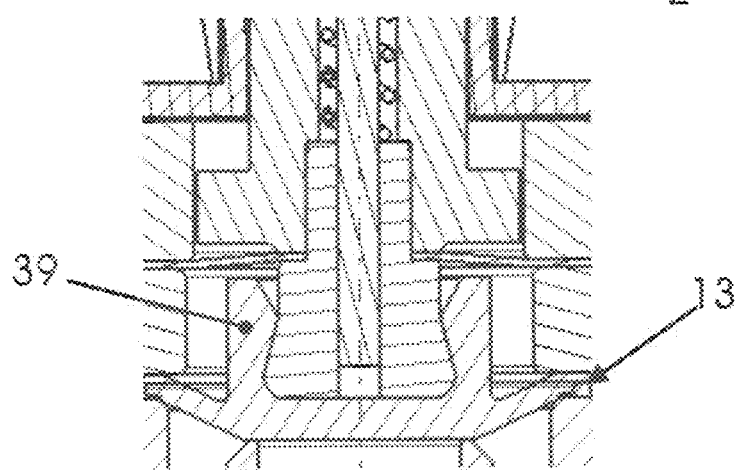
Figure 23:
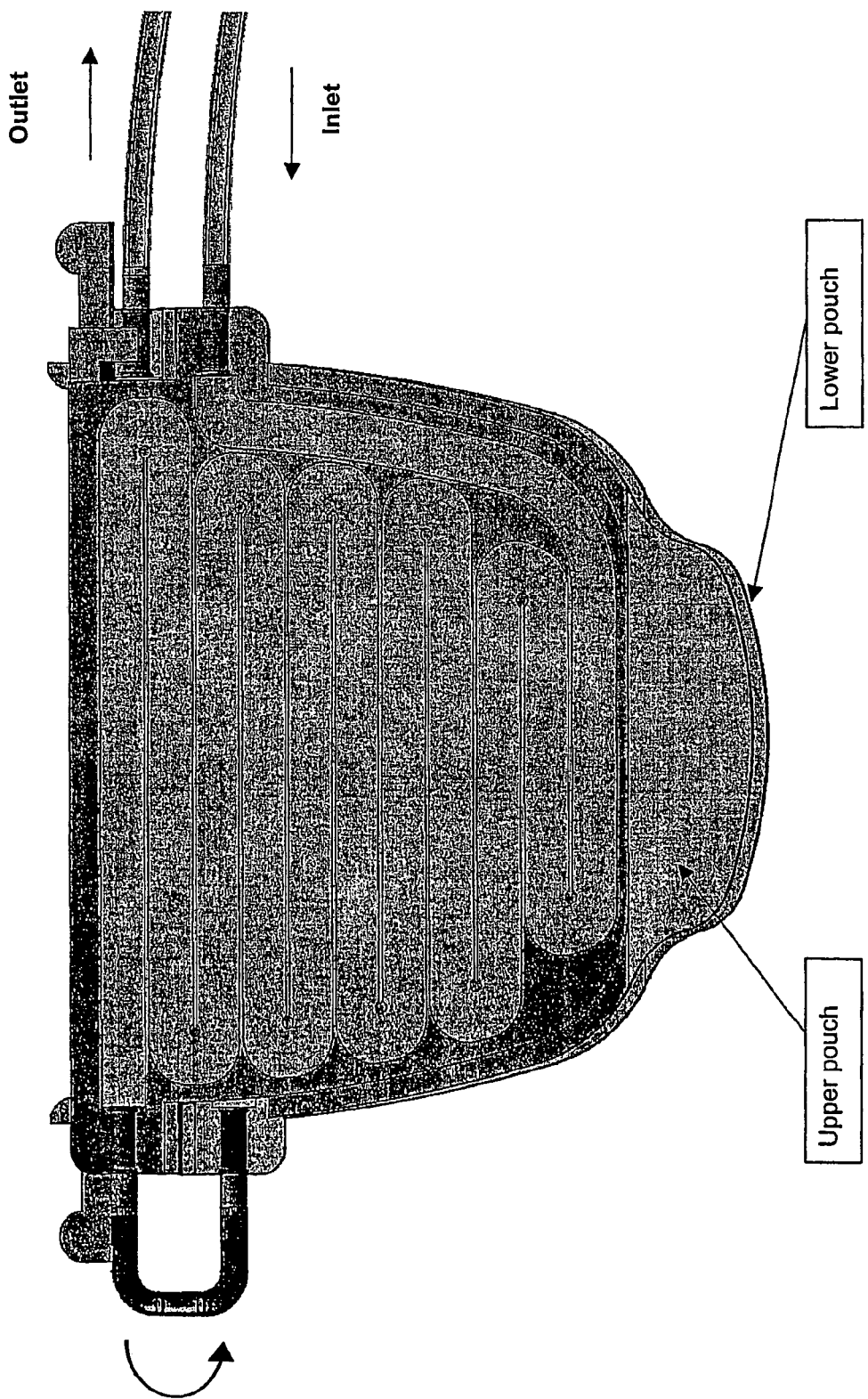
Figure 24A:
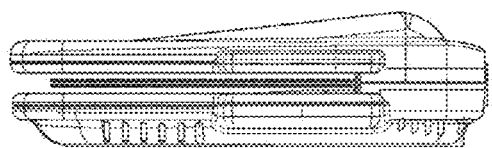
Figure 24B:
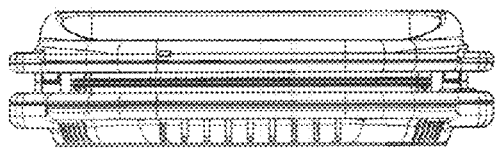
Figure 24C:
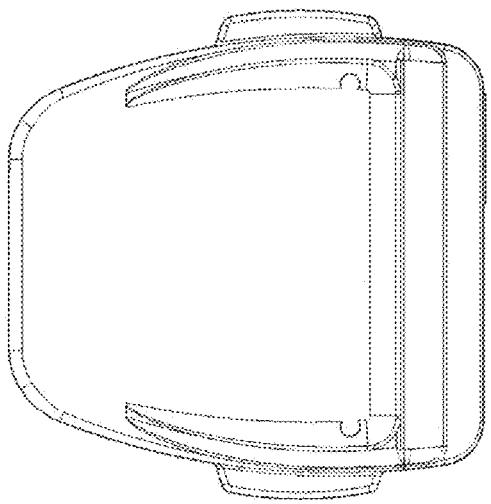
Figure 26:
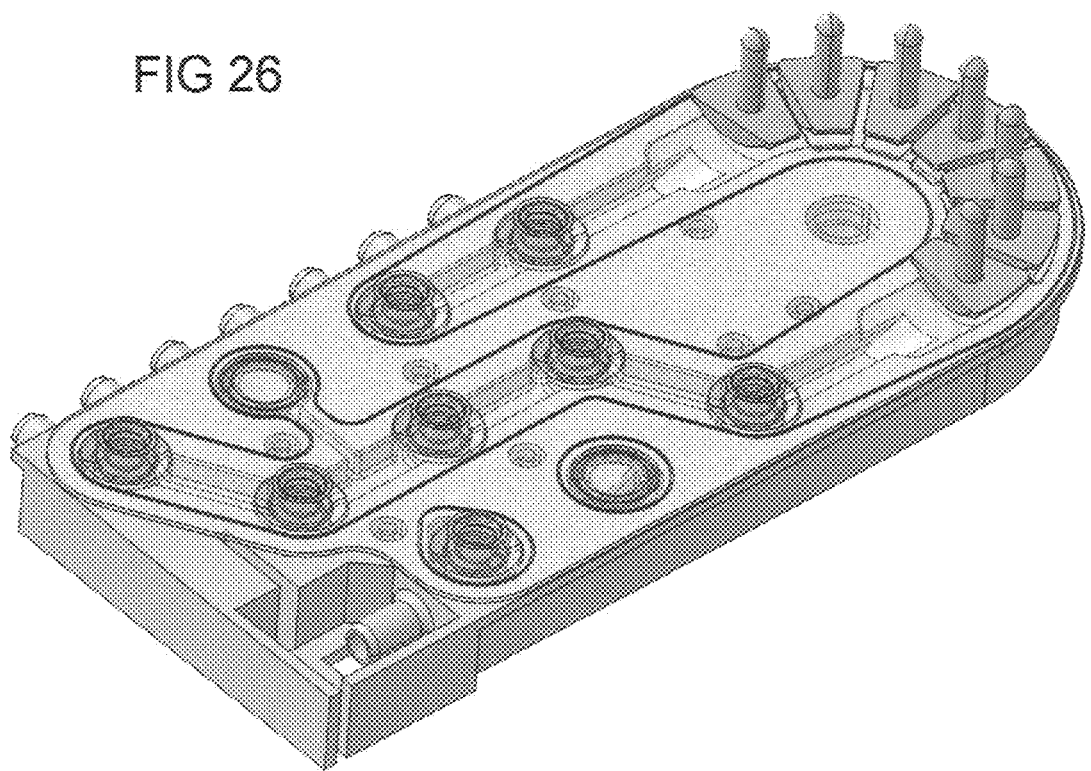
Figure 27:
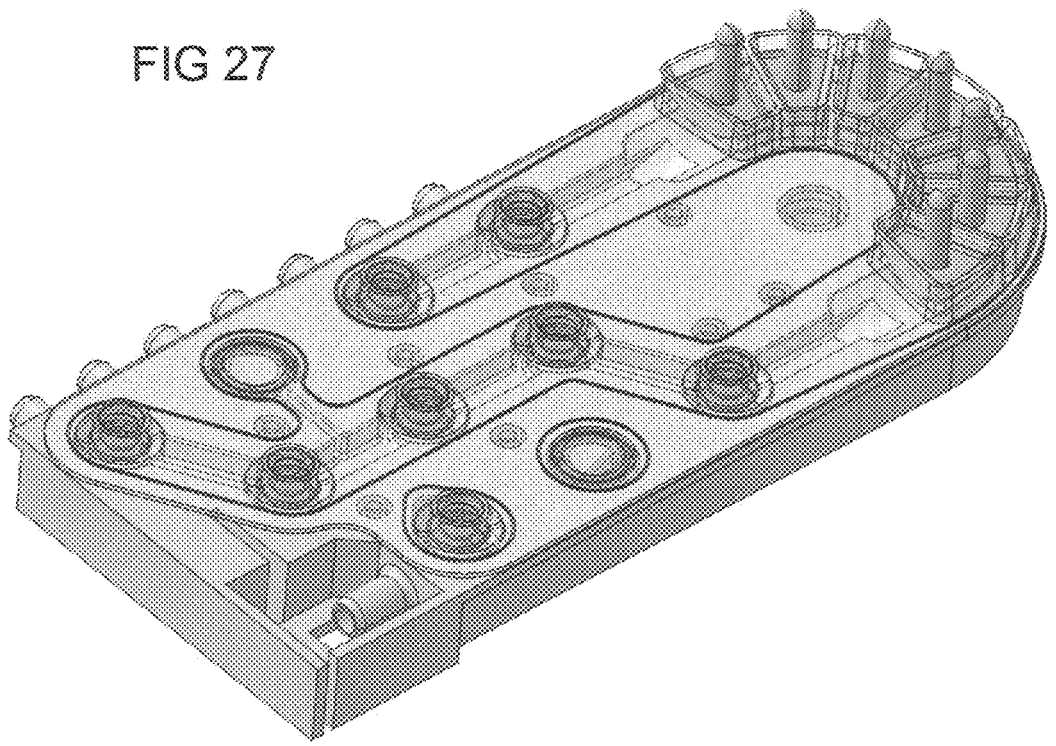
Figure 28:
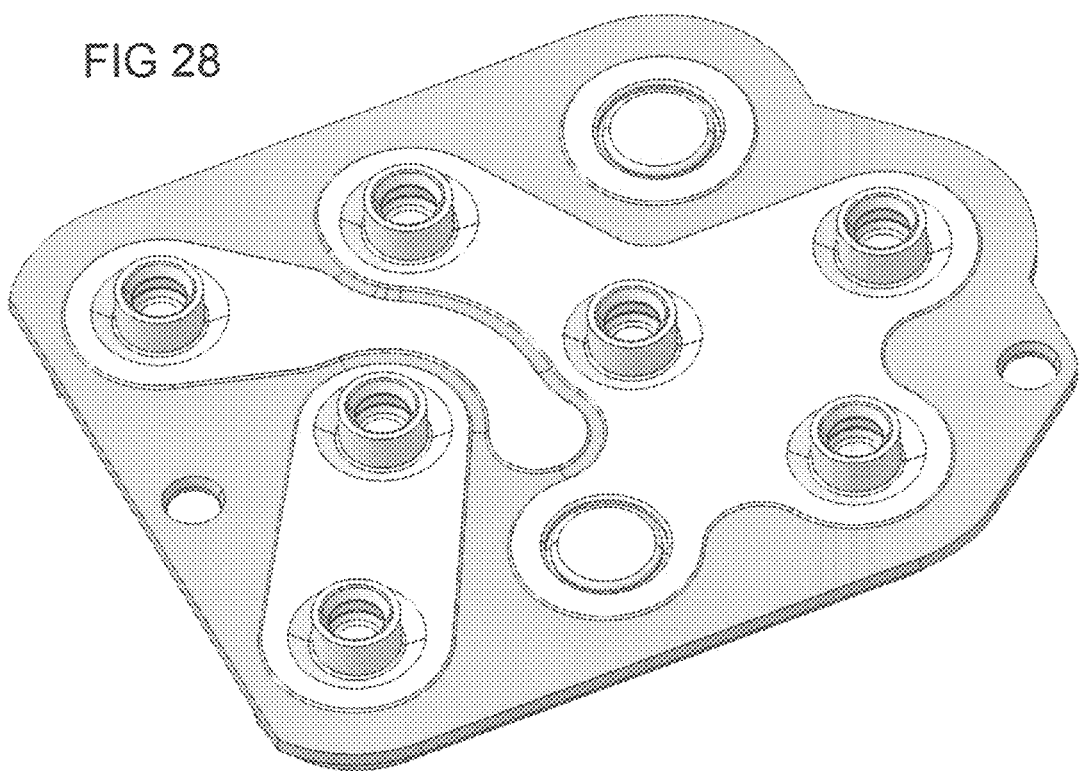
Figure 29:
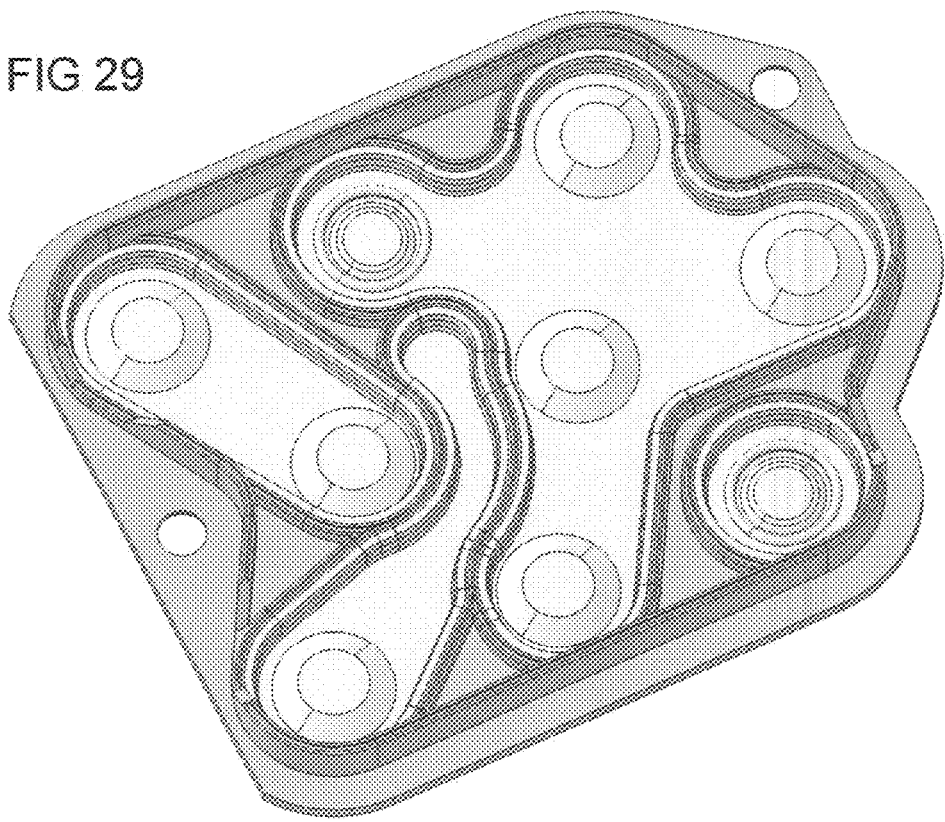
Figure 30:
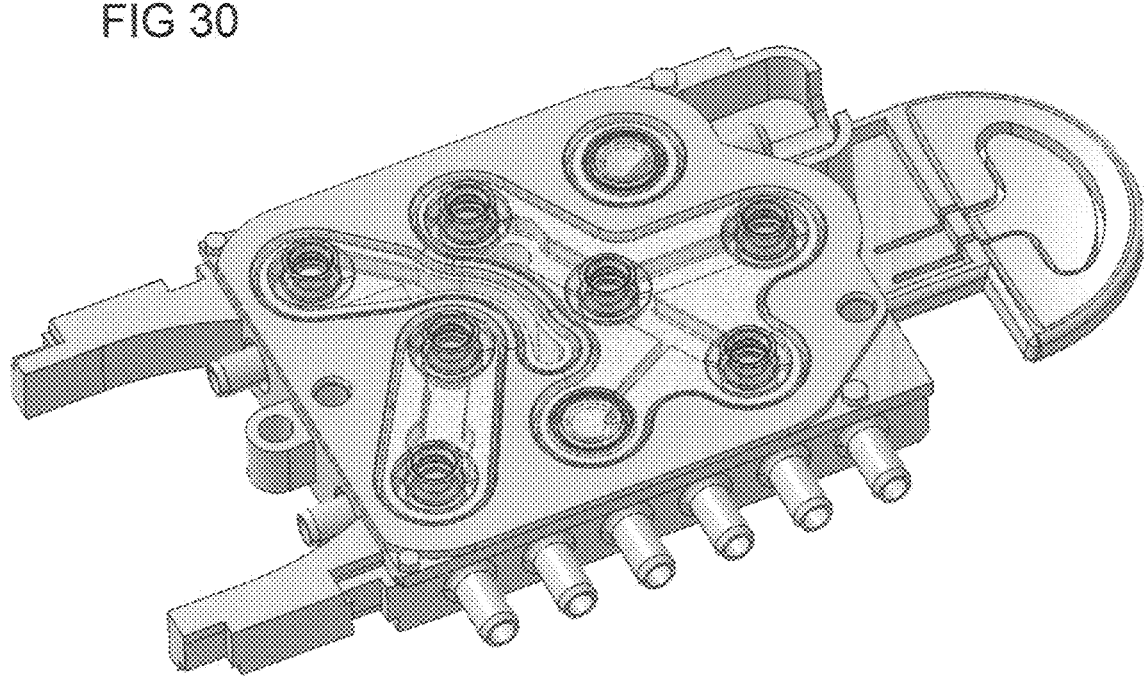
Figure 31:
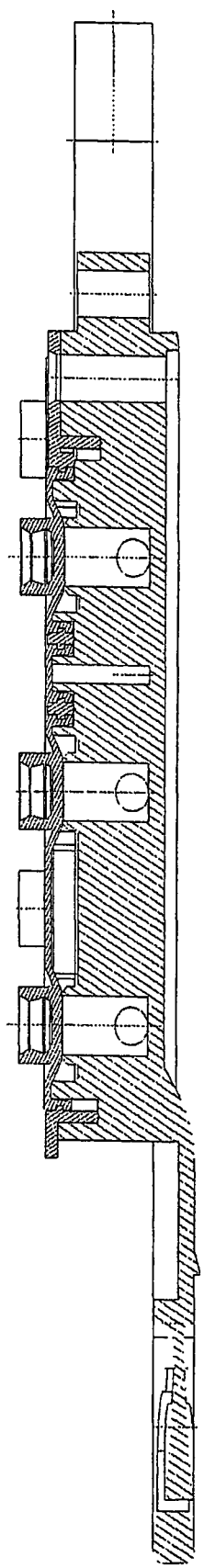
Figure 32:
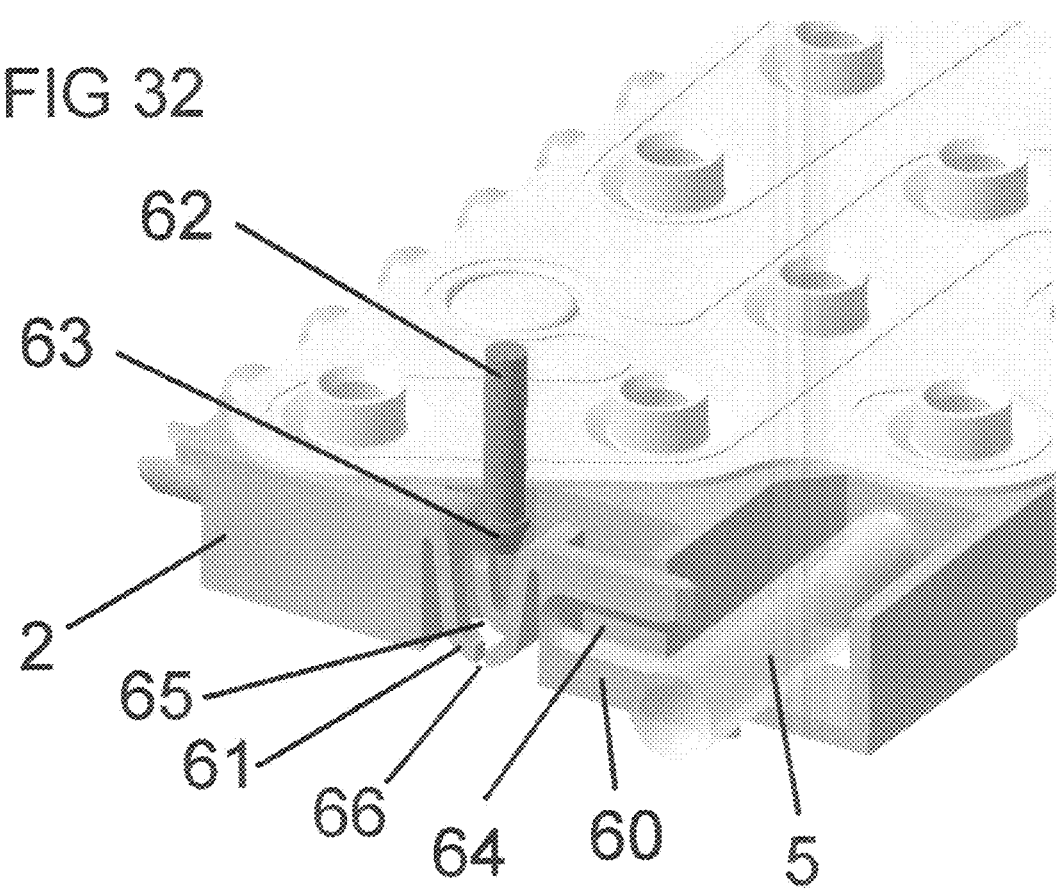
Figure 33:
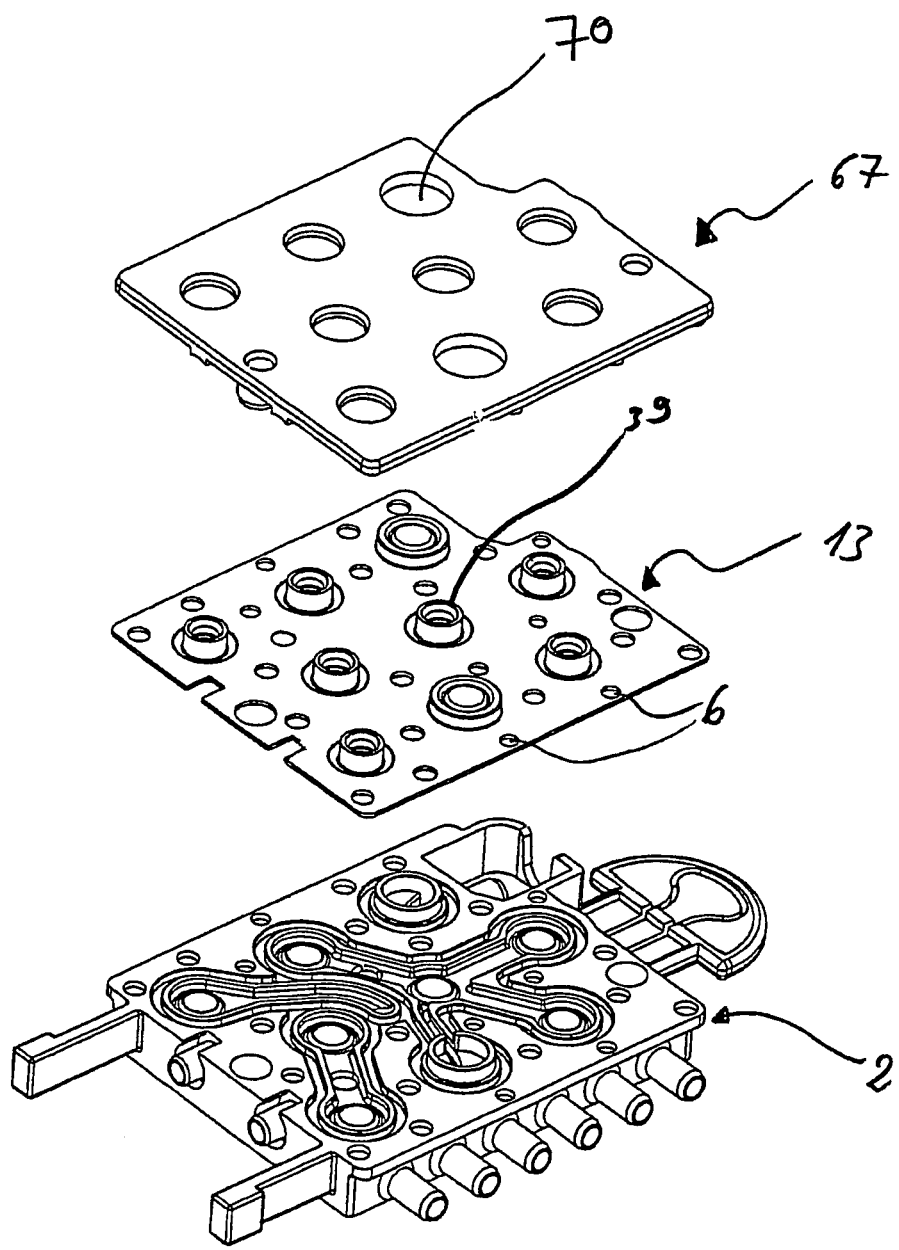
Figure 34:
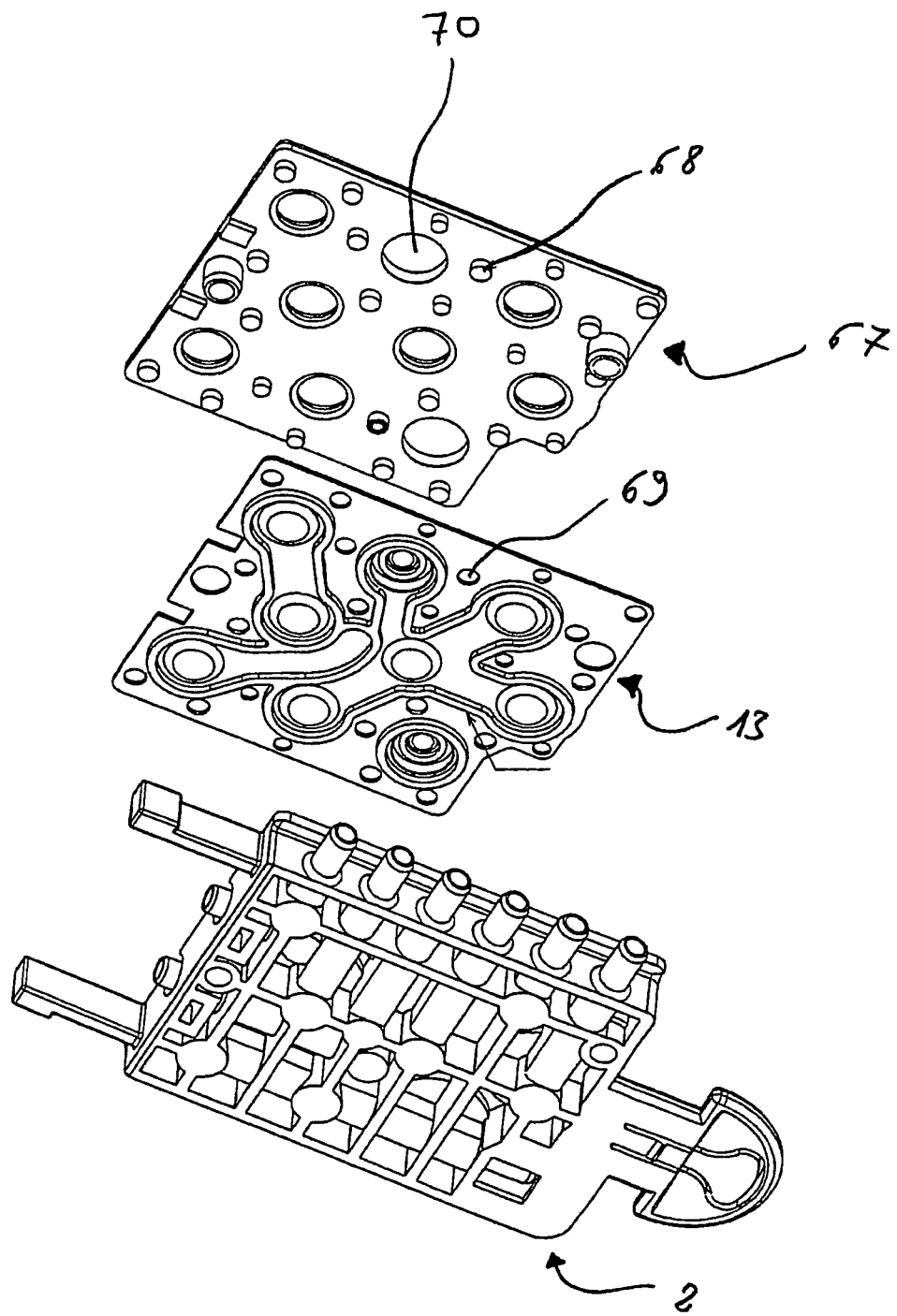
Figure 35:
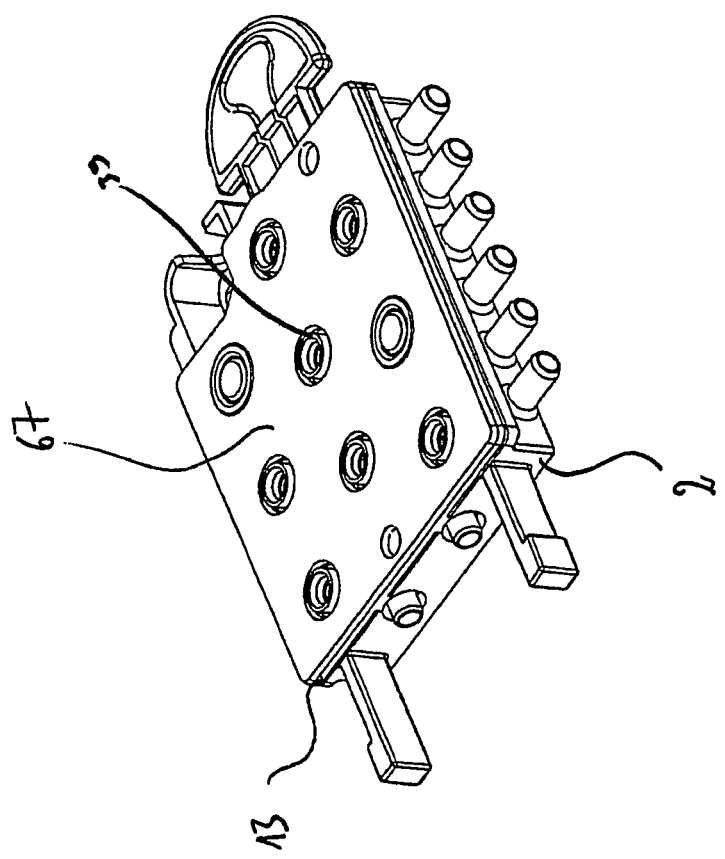
Figure 36:
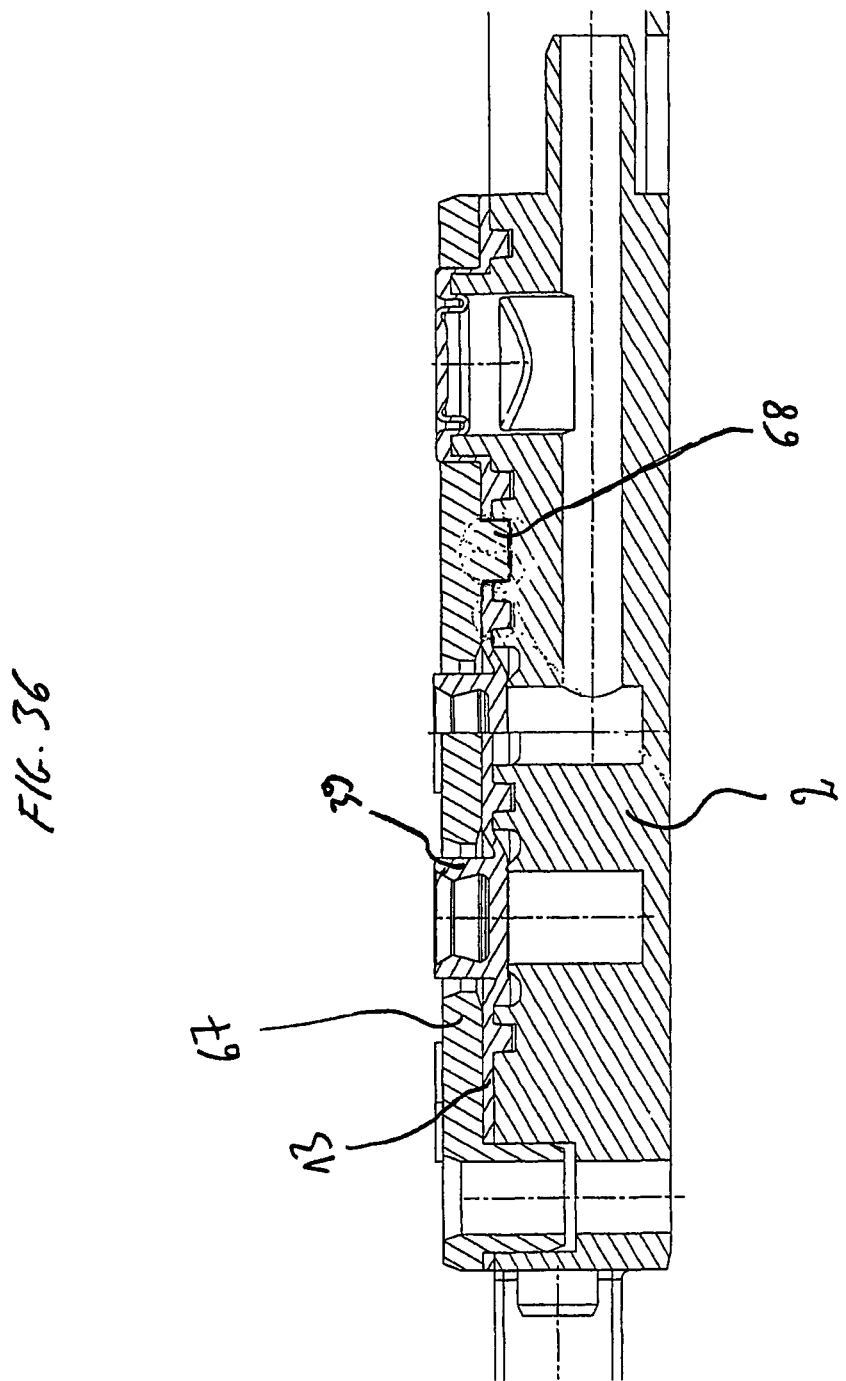

FIG. 17 shows the cycler of FIG. 10, the insertion slot opened with the cartridge FIG. 18 shows the cycler of FIG. 10, the insertion slot closed with the cartridge FIG. 19 shows a front view of a valve FIG. 20 shows a front view of a pressure sensor FIG. 21 shows a pump race FIG. 22 shows a valve actuator and a membrane clipping system FIG. 23 shows a warmer FIG. 24 shows a warmer casing FIG. 25 is a table showing drain profiles FIG. 26 shows another embodiment of the invention FIG. 27 shows another embodiment of the invention FIG. 28 shows a molded frame in an upper view FIG. 29 shows the molded frame of FIG. 28 in a bottom view FIG. 30 shows the molded frame of FIG. 28 fixed to a liquid distribution system FIG. 31 shows the system of FIG. 30 in a cross section FIG. 32 shows a flow preventing system FIG. 33 shows an exploded upper view of another embodiment of the invention FIG. 34 shows the embodiment of FIG. 33 in a bottom view FIG. 35 shows the embodiment of FIGS. 33 and 34 in an assembled view FIG. 36 shows a cross section of the embodiment of FIG. 35

Figure 37:
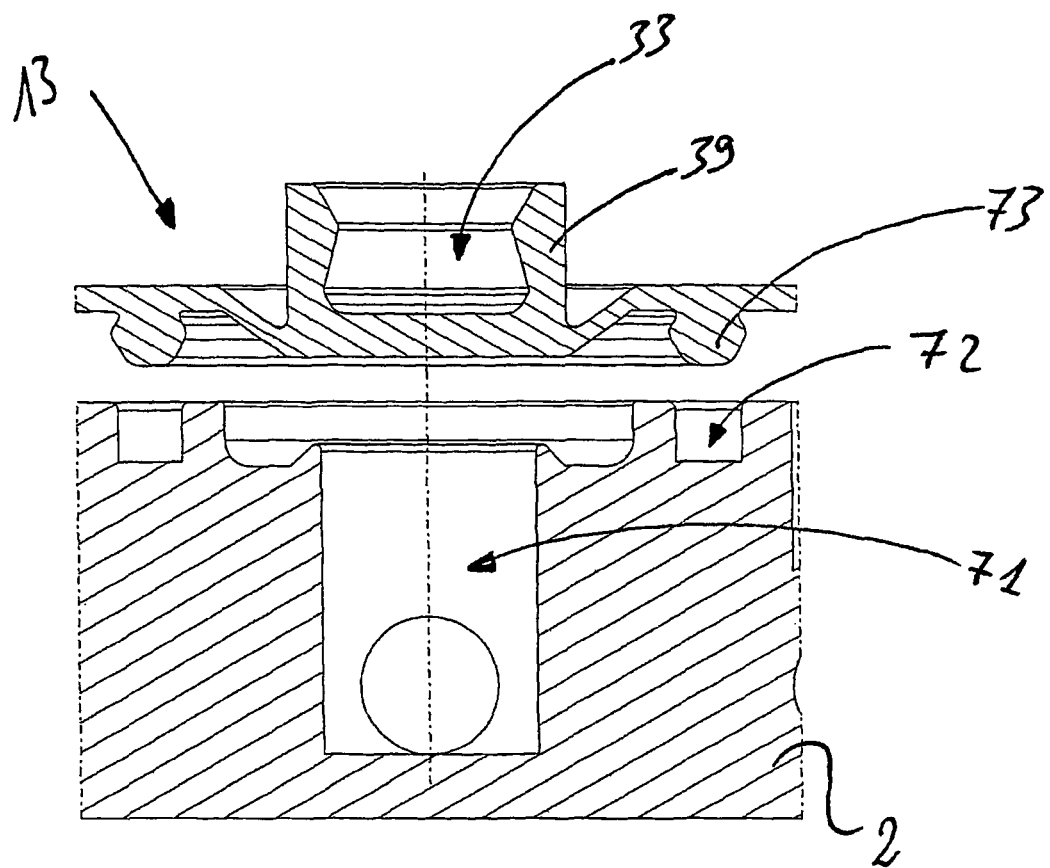

FIG. 37 shows an enlarged view of a part of the embodiment of FIG. 33.

NUMERICAL REFERENCES USED IN THE DRAWINGS

1. Pump
2. Liquid distribution system (cartridge)
3. Supply means (bag)
4. Patient
5. Patient line
6. Drain collector
7. First hub chamber
8. Second hub chamber
9. Liquid supply port with valve
10. Patient port with valve
11. Drain port with valve
12. Roller separator
13. Membrane
14. Membrane frame
15. Pressure sensor cavity (patient)
16. Patient port with valve (warmer chamber)
17. Warmer chamber
18. Patient port with valve (first hub chamber)

19. Warmer port
20. Roller element
21. Pump race
22. Roller
23. Tube connector for warming enter line
24. Liquid supply line
25. Drain line
26. Pump inlet
27. Pump outlet
28. Warmer pouch
29. Warmer enter line
30. Warmer exit line
31. Membrane pressure sensor area
32. Retaining element for pressure sensor
33. Clip cavity
34. Actuator
35. Clip plunger
36. Pressure sensor cavity (first hub chamber)
37. Pump flexible tube
38. Warmer port with valve
39. Membrane actuator clip
40. Membrane pressure volute
41. Cartridge loader
42. Pump motor+coder
43. Air sensor
44. Pressure sensor
45. Pump casing
46. Cartridge loader shaft
47. Cartridge loader frame
48. Cartridge loader linear cam
49. Cartridge loader motor
50. Cartridge insertion slot
51. Cycler
52. Cartridge motor shaft
53. Tube connector for supply line
54. Tube connector for drain line
55. Tube connector for warmer exit line
56. Pump enter line
57. Pump exit line
58. Sensor pressure housing
59. Sealing flange
60. Clamping member
61. Shaft retaining member
62. Shaft
63. Retaining lip
64. Clamping slot
65. Opening
66. Releasing slot
67. Rigid plate
68. Pin
69. Membrane holes
70. Rigid plate holes
71. Cavity
72. Groove
73. Flange

DETAILED DESCRIPTION OF THE INVENTION

The peritoneal dialysis system according to the invention is shown in a schematic way in FIG. 1. It includes a pump 1, a liquid distribution system 2 (also named cartridge) comprising a first hub chamber 7 and a second hub chamber 8. The first chamber 7 includes a pump inlet 26 connected to the pump 1 via a pump enter line 56, a liquid supply port 9 with valve connected to supply means, e.g. to bags 3, via a liquid supply line 24 and a patient port 10 with valve connected to a patient 4 via a patient line 5. The second chamber 8 includes a pump outlet 27 connected to the pump 1 via a pump exit line 57, a drain port 11 with valve connected to a drain collector 6 via a drain line 25 and a patient port 18 with valve connected to a patient 4 via a patient line 5.

FIG. 1A shows the "fill" phase where liquid is supplied to the patient 4 from and through the following elements: Bag 3—Liquid supply line 24—(open) liquid supply port 9—First chamber 7—Pump inlet 26—Pump enter line 56—Pump 1—Pump exit line 57—Pump outlet 27—Second chamber 8—(open) Patient port 18—Patient line 5—Patient 4.

Figure 1B:
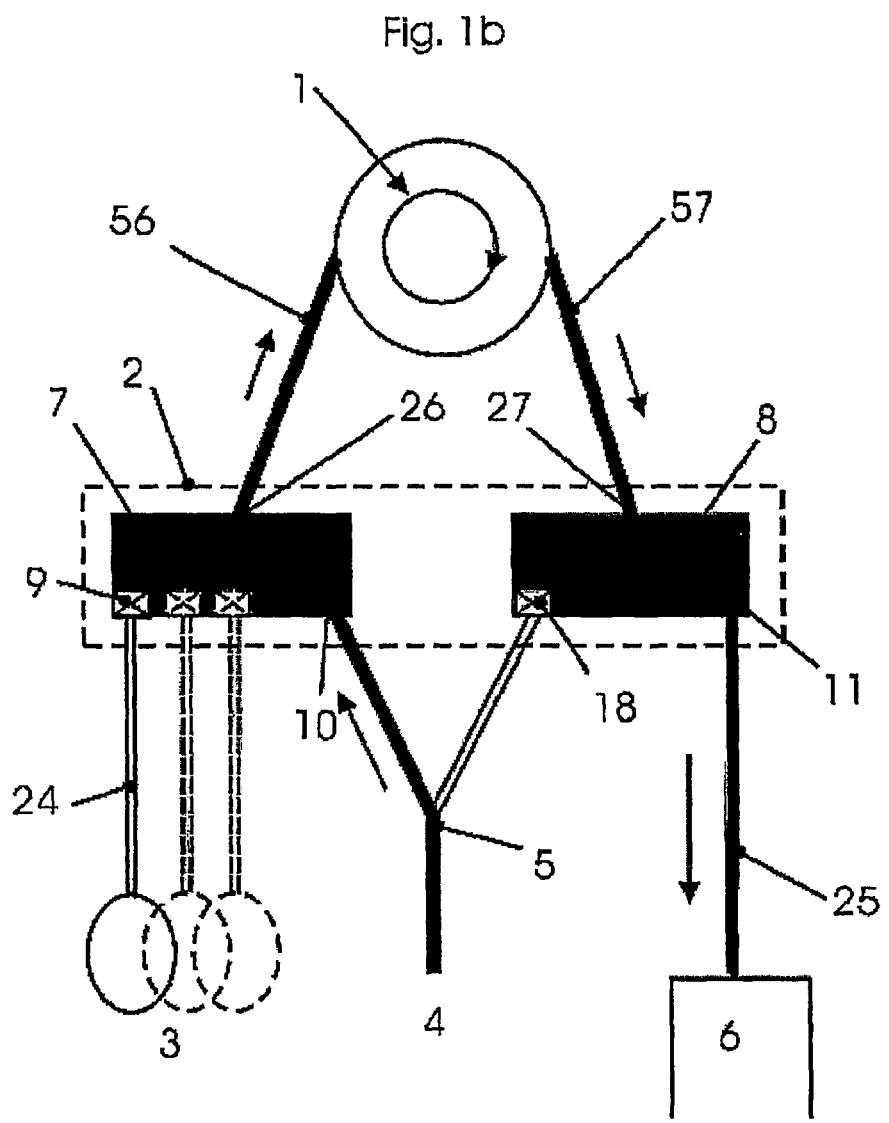
FIG. 1B shows the "drain" phase

FIG. 1B shows the "drain" phase where liquid is drained from and through the following elements: Patient 4—Patient line 5—(open) Patient port 10—First chamber 7—Pump inlet 26—Pump enter line 56—Pump 1—Pump exit line 57—Pump outlet 27—Second chamber 8—(open) Drain port 11—Drain line 25—Drain collector 6.

The embodiment illustrated on FIG. 2 shows an assembly constituted by a pumping element 1 and a cartridge 2. Both elements are fixed together but may be separated. FIG. 21 shows a better view of the fixation between both elements. Preferably, the pumping element 1 is fixed to the cartridge 2 by vibration attenuation means in order to minimize the vibration on cartridge 2 when the pump is operating.

The upper face of the cartridge contains a first hub chamber 7, a second distinct hub chamber 8 and a cavity 15 which forms part of a pressure sensor. The first chamber hub chamber 7 has three liquid supply ports 9, one patient port 10, one pump inlet 26 and a cavity 36 which forms part of a pressure sensor. The second hub chamber 8 has a patient port 18, a drain port 11 and a pump outlet 27.

The pumping element 1 comprises a pump casing 45 which contains three rollers 22 maintained around the pump casing center by a roller separator 12. The space between the roller-roller separator element and the pump casing defines a pump race 21 in which a flexible tube 37 is placed. The flexible tube being connected with the pump enter 56 and exit 57 lines. The rollers 22 may be motor driven by a shaft 52 (not shown on FIG. 2) in such a way as to progressively compress the flexible tube 37 resulting thereby in a peristaltic movement along the flexible tube 37.

During the "fill" phase, liquid is supplied via one tube connector 53 and liquid supply port 9 to the first hub chamber 7. It then enters the pump 1 through the pump inlet 26, moves along the flexible tube 37, enters the second hub chamber 8 through the pump outlet 27 and goes to the patient 4 via patient port 18 and patient line 5.

During the "drain" phase, liquid leaves the patient 4, enters the first hub chamber 7 via patient port 10. It then enters the pump 1, moves along the flexible tube 37, enters the second hub chamber 8 and goes to the drain collector 6 via drain port 11, drain tube connector 54 and drain line 25.

It should be noted at this stage that each bag 3 may contain a specific liquid.

The cartridge 2 of FIG. 3 is identical to the cartridge of FIG. 2 with the exception of an additional cavity, namely a warmer chamber 17, which includes a warmer port 19 and a patient port 16. The warmer port 19 is connected to a warmer 28 (not shown on FIG. 3) via a warmer tube connector 55 and a warmer exit line 30. The patient port 16 is connected to the patient line 5. The second hub chamber 8 contains a warmer port 38 connected to a warmer 28 (not shown on FIG. 3) via a warmer tube connector 23 and a warmer enter line 29.

During the "fill" phase, liquid is supplied via one tube connector 53 and liquid supply port 9 to the first hub chamber 7. It then enters the pump 1, moves along the flexible tube 37, enters the second hub chamber 8, moves into the warmer 28 via warmer port 38, enters the warmer chamber 17 via warmer port 19 through the tube connector 55 and goes to the patient 4 via patient port 16 and patient line 5.

As it can be seen on the embodiments of FIGS. 2 and 3, the pump 1 is unidirectional, i.e. whatever the pumping phase is, liquid in the flexible tube 37 always moves in the same direction. This feature provides several advantages. In particular a higher precision in the liquid exchange due to the same flow speed for both the fill and drain phases and a longer life time.

It is known that peristaltic pumps are usually accurate within +/− 5%. As such, peristaltic pumps cannot be used for peritoneal dialysis since the volume which is filled within the patient cavity requires to be drained in the same amount within +/− 2%, otherwise the peritoneal cavity could be overfilled (e.g. for 12 liters exchanged over the therapy, a 3% difference represents 360 ml which is as much as 18% of the 2 liters contained in the peritoneal cavity for each cycle) and/or the ultra-filtration could be altered. In order to improve on the accuracy of the exchanged volume without requiring the construction of highly accurate pumps which would warranty a +/−2% accuracy, the invention provides a method whereby the conventional pump is used in a unidirectional way which insures the same accuracy for both the fill and the drain phase (usually within +/−2%) and therefore an appropriate balance of fluid. The volume filled with such a pump may be inaccurate within +/−5%, but since the same cassette with the same flow speed characteristics (namely the same flow direction) is used, the balance can be insured within +/−2% as required for the therapy. If the cassette would be used in both directions, the difference in flow speed would be within +/−5% due to the non parallel behavior of peristaltic pumps, in particular over time.

It should be noted that with the present invention, the precision in the liquid exchange is maintained even if the pump flow rate changes after a certain time due to aging of the tubing since the fill and drain are operated within a time window which is small in comparison to the time in which the flow speed is altered by aging (e.g. a flow alteration of the pump of approximately 1% per 20 liters of fluid pumped, with exchanged volumes of approximately 2 liters per cycle). In addition, the use of the cassette in one direction enables a better control over the aging of the tubing and, therefore, a better prediction of the impact on the pumping accuracy.

Figure 4:
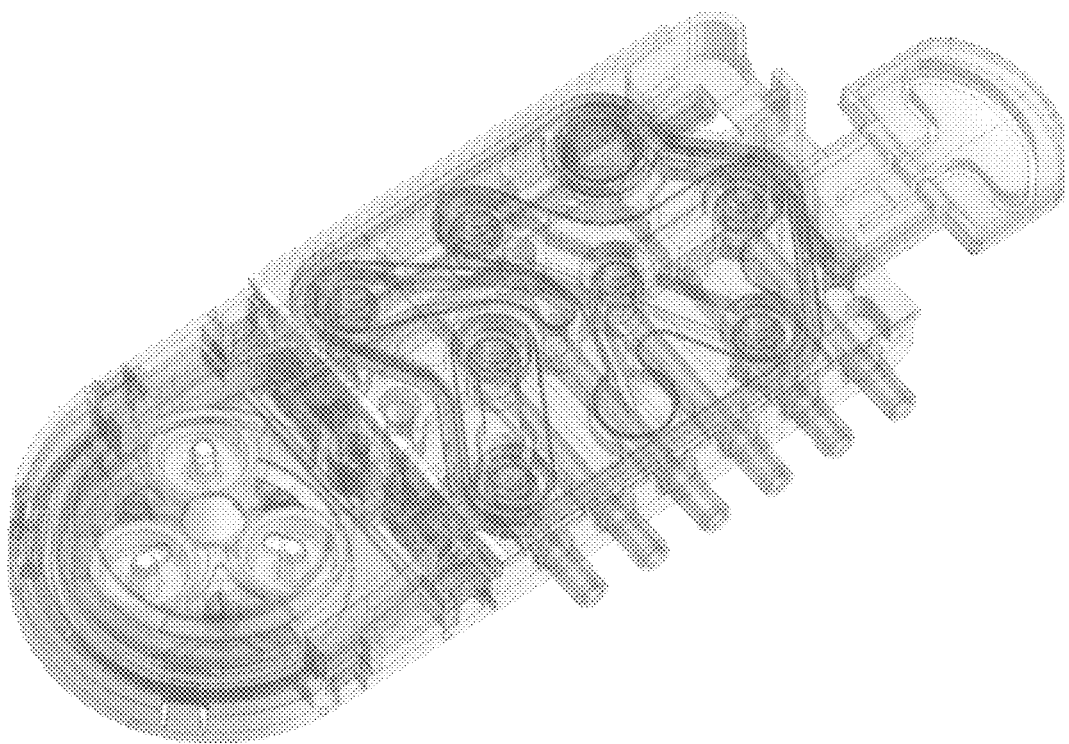
FIG. 4 shows the embodiment of FIG. 3 in a transparent view
Figure 5:
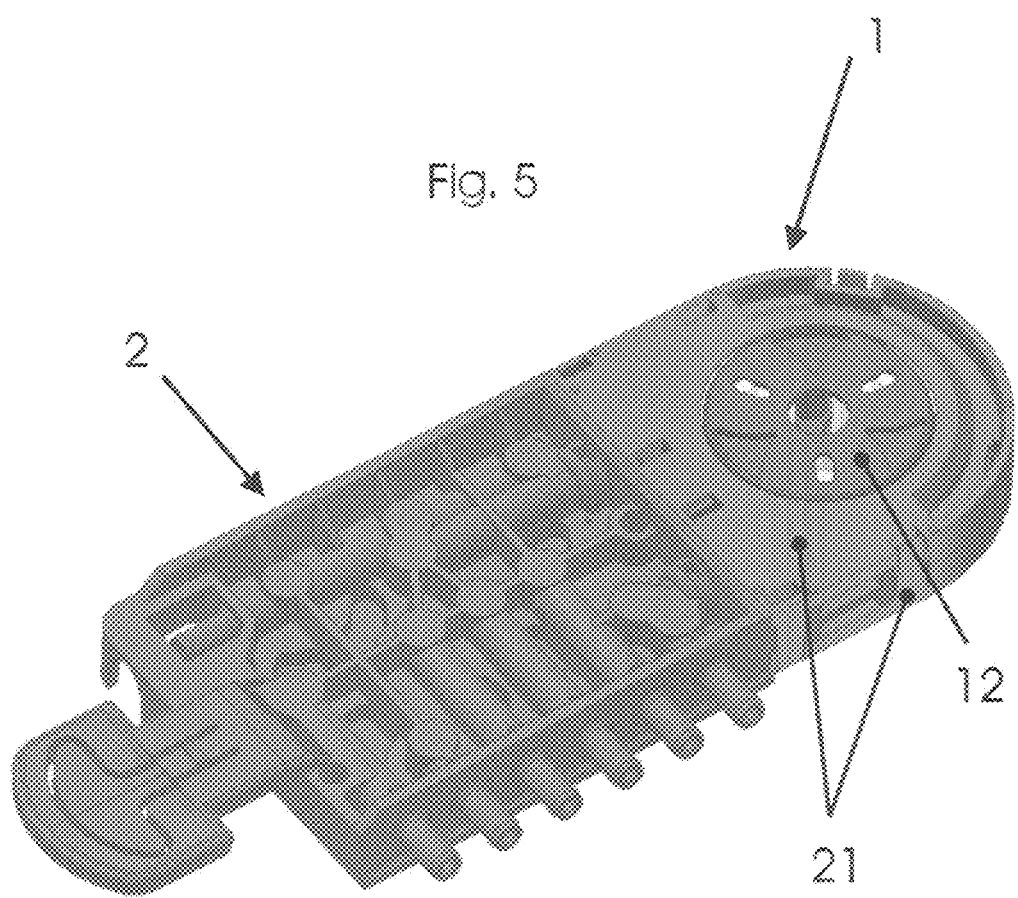
FIG. 5 shows the back side of the embodiment of FIG. 3 (disposable cartridge)

FIG. 4 is a transparent view of the cartridge which better shows how the different elements are connected. A cartridge bottom view is shown on FIG. 5. The tubing system in the lower face and the cavities of the upper face are all made within one single part, e.g. an injected part of plastic material.

FIG. 6 shows an assembly including the cartridge 2 of FIG. 3 fixed to a pumping element 1, a patient line 5, supply bags 3, a warmer enter line 29, a warmer outer line 30 and a warmer pouch 28 which is essentially made of a fluid circuit within a plastic bag (e.g. PVC) to be put into contact with a warming plate.

FIG. 6" shows a warming plate contained into a warming system where the warming pouch has a shape of a sock to be inserted onto the warming plate. The warming pouch is composed of a liquid channel which forces the liquid to be maintained within such warmer for a certain duration at a given flow rate.

FIG. 7 shows a cartridge identical to the one of FIG. 3 where the rollers are part of the cycler rather than of the cartridge. In this embodiment, the pumping element 1 which only contains the tube and tubing race and the cartridge 2 are forming a single element.

The rollers, which are part of the cycler and therefore re-usable rather than disposable with the cartridge, have a conical shape so as to allow the rollers to be self inserted in the pump race. In this configuration the cartridge is more simple to manufacture and contains less parts. No other insertion mechanism is required, since the tube is automatically compressed on the race while the rollers are penetrating into the cartridge. As a separate matter, the use of conical rollers 22 results in a more constant speed of the liquid along the flexible tube 37.

FIG. 8 shows the assembly of FIG. 7 without the rollers 22 and the roller element.

Of course, other roller shapes may be used, e.g. spherical or cylindrical.

The embodiment of FIG. 9 only differs from the one of FIG. 8 in that the pump casing 45 is made out of two parts with an interface between the pumping element 1 and the cartridge 2. This configuration offers an improved assembly process of the pump and the possibility to add means to limit the propagation of the vibrations from the pump 1 to the cartridge 2.

FIG. 10 shows a cycler 51 without cartridge 2 and pumping element 1. It contains a driving zone which includes a motor shaft 52 for the rollers 22 and several actuators 34. The cycler 51 also includes an air sensor 43 situated close to the patient line 5 when the cartridge 2 is inserted. The air sensor may be made of a piezo emitter and a piezo receiver.

FIG. 11 represents the embodiment of FIG. 2 with a flexible membrane 13 covering the hub chambers 7,8 and the pressure sensor cavity 15.

The upper face of the membrane 13 (see FIG. 12) contains several valve elements having a cylindrical cavity 39 and a pressure sensor area 31 with a ply 40 around its periphery. The valve elements 39 are designed to tightly close the ports when the membrane 13 moves downwardly.

On its bottom face (see FIG. 13) the membrane 13 contains a semi-circular flange 32 around the pressure sensor area and annular liquid tight joints.

In addition the cartridge 2 includes liquid tight joints arranged in such a manner that they allow a liquid tight connection between the cartridge 2 and the membrane 13.

Advantageously the membrane is molded. Preferably the membrane 13 is made of silicone.

The membrane 13 is press-fitted to the cartridge 2 along its periphery with a membrane frame 14 (see FIG. 14).

FIG. 15 shows the cycler of FIG. 10 in an open state which includes a pump motor and a coder 42. The rectangle 41 represents the cartridge loader.

FIG. 16 shows a cartridge loader comprising cartridge loader shafts 46, a cartridge loader frame 47, a cartridge loader linear cam 48 and a cartridge loader motor 49. On this figure, the two displacement parts 48' and 48" represent two different positions of the loader in an open and closed position only for explanation reasons.

The cartridge loading mechanism allows a tight connection between the membrane and the valves and the cartridge. In order to insure proper positioning of the cartridge onto the valve actuators, as well as pressure sensor and air sensor onto the right place, the cartridge is maintained into the loading mechanism which progressively moves the cartridge in an axis which is perpendicular to its surface. By the same movement, the axis or the rollers can be inserted in the right position to ensure proper functioning of the pump. The same movement can also insure appropriate pressure on the surfaces which requires to be maintained together, such as for tightness control on the membrane and/or tubing of the pump.

FIG. 17 shows the cycler 51 of FIG. 10 containing a cartridge 2. The cycler 51 has an insertion slot 50 in an open position.

FIG. 18 shows the same cycler 51 but with an insertion slot in a closed position.

FIG. 19 represents an actuator 34 with its plunger 35 clipped in its corresponding valve element 39 of the membrane. The actuator 34 may be a magnet or an electromagnetic element. The plunger 35 and the valve element 39 are designed to move together when the actuator is activated.

FIG. 22a and 22b shows the plunger 35 and the valve element 39 in a separate position (FIG. 22a) before insertion and in an activated position (FIG. 22b) after insertion. One embodiment of the invention is to insure a proper insertion of the actuator head into the membrane clipping part by having the length of the part of the actuator head to be inserted into the clip of the membrane to be longer than the possible displacement of the actuator head, so as to ensure that the actuator head is always properly inserted into the clip of the membrane. As such, in the worst case where the actuator head would be fully retracted within the actuator during the clipping translation into the membrane, the actuator head would pass the clipping equilibrium position before the end of the translation, so that the remaining translation will ensure clipping of the actuator head into the membrane.

The front view of FIG. 20 illustrates a pressure sensor 44 which may be used with the independent pressure sensor cavity 15 of the cartridge 2 or with the pressure sensor cavity 36 of the first hub chamber 7. The ply 40 makes the pressure sensor less sensitive to the elasticity of the membrane 13 in the sensor pressure area. In addition, the shape of the cavity 15 shall be made such that air can be eliminated easily when fluid is passing into the cavity (e.g. by having a round shaped bottom of the cavity within the direction of the flow).

In the embodiments discussed previously, each port has a dedicated valve. This is not the case for the pump inlet and the pump outlet which are always kept open.

The invention encompasses several other features not necessarily illustrated on the figures. For instance, the cycler or the cartridge-pumping element assembly may contain a window for detecting correct positioning of the flexible tube of the pump as shown in FIG. 21 (circle).

When the system functions, the pressure is preferably always maintained positive with respect to the drain. This is a safety measure which avoids said contaminated liquid to potentially infect the patient.

Advantageously the liquid pressure entering and exiting the cartridge is sensed and, if necessary, the pump flow rate is corrected in accordance with the pressure difference. This pressure difference is better calculated at the initial priming phase of the system, where the pressure is directly related to the positioning of the liquid bags 3 and the patient position relative to the cycler.

Alternatively or in addition, the pump flow rate may be regulated according to a predetermined deterioration of the tubing which is known from the characteristics of the tubing.

The drain phase may be limited as to its duration in function of the drain speed, the drain speed having to be reduced when the patient peritoneal cavity pressure decreases, typically between 30 ml/min and 120 ml/min instead of a nominal 200 ml/min speed. This feature is particularly interesting because the dialysis efficiency is directly related to the time the liquid stays in the peritoneal cavity and the duration required to fully drain the peritoneal cavity may limit this time without a significant impact with regard to the peritoneal fluid characteristics. As such, one method of the invention would be to determine at which speed it is not worth continuing draining the patient entirely and rather fill the patient with fresh fluid, taking into consideration the remaining fluid volume in the peritoneal cavity which has not been expelled and expected ultra-filtration additional volume to avoid overfill. The cycles will therefore be all different, based on reaching a pre-determined drainage speed or a pre-determined decrease profile of the drainage speed, so that the efficient time of dialysis will be increased. An example of drainage speed on a patient is given in the FIG. 25, where, for each column which is divided in three parts, the upper part corresponding to a limit of drainage speed at which it is, for example, not worth continuing the drainage even if the next fill volume will not be a full fill. In comparison to actual method where a tidal at (e.g. 80%) is preset, the method under the invention is adapting each drainage to the actual drainage speed, trying to empty as much as possible without compromising on the efficacy of the peritoneal dialysis. Of course some limits can be set, where a minimum of drainage volume has to be reached before such a limitation takes place for each cycle.

Another method under the present invention consists to fill always as much volume, within certain limits to be set for the patient, until a certain pressure in the peritoneal cavity is reached. As such, the peritoneal dialysis can be improved since the efficiency is related to the amount of fluid filled at every cycle. According to such method, the pump shall fill the patient until a certain pressure is reached (e.g. 10 cm water) and stop only once such pressure is reached or a certain maximum volume is reached. Accordingly, it is important to measure continuously the pressure during the dwell time to make sure that no over pressure is reached, such as due to the ultra-filtration. One possibility is also to always fill up to such a limited pressure and/or volume and drain at a certain interval thereafter a certain volume to compensate for expected ultra-filtration. Another possibility is to increase the ultra-filtration during the last cycle, by using e.g. low sodium concentrated solution.

FIG. 26 illustrates another embodiment which uses peristaltic finger elements working on a hemispheric channel in the hard plastic part. The channel and the liquid distribution system are covered by a single membrane. A peristaltic pumping effect is obtained by pressing down these fingers in a sequence. This performs a digital type peristaltic pump with a high accuracy, which remains in particular independent of inlet and outlet pressure changes. Preferably the fingers are moved in a progressive way to simulate a peristaltic movement. Those fingers can be operated either individually, e.g. by electric means, or by a mechanical cam which simulates the peristaltic movement and which is rotating along the fluid channel (e.g. a rotating disk with a variable thickness which displays a wave on its surface in contact with the finger elements). Alternatively, those fingers can be clipped onto the membrane and be operated individually in the same manner as the valves are, or by a rotating disk cam. In such last embodiment, the advantage is that the position of the membrane is perfectly known in both push and pull direction, to ensure that the peristaltic pumping is not depending on the pressure.

The embodiment of FIG. 27 only differs from the embodiment of FIG. 26 in that the membrane includes cavities to receive and guide the finger elements (e.g. by clipping means).

Preferably the membrane is biocompatible, allows a simple sealing to the liquid distribution system e.g. by welding, sticking, gluing, laser or heat melting. In addition the membrane should be made in a material avoiding the release of particles due to mechanical stress or self migration due to the material itself (e.g. Kraton™, Santoprene™, Biopure™, Pebax™ or Polyurethane). Finally the membrane must be soft and elastic in order to properly perform valve and/or pump functionalities.

It is also possible to use multi-layer material with in inner layer (on the fluid side) which is more biocompatible and with low spallation characteristics.

In one particular embodiment, the membrane is also covering the fluid pumping channel, at 45°, to ensure possible operation with either conical rollers or ball rollers which are part of the cycler.

FIGS. 28 to 31 illustrates a molded frame which is adapted to cover in a tight manner the space between the hub chambers, each space above said hub chambers being covered by a flexible membrane, preferably made of injected silicone or elastic biocompatible material. In such embodiment, the molded frame and silicone or elastic biocompatible membrane can be obtained by over-molding techniques.

The system according to the present invention may furthermore include free flow preventing means which prevent the flow of fluid towards or from the liquid distribution system when it is released from the cycler.

This preventing means may be made of a mechanical clamp around the patient line, which is not clamping during the treatment will be closed automatically due to the movement of a loading mechanisms by releasing the cartridge, such as by clipping mechanism.

FIG. 32 illustrates such a clamping mechanism which consists of a slotted clamping member 60 movably fixed to the liquid distribution system 2 via a flexible U shape member 61. FIG. 32 also shows a shaft 62 which is fixed to the cycler (not shown). In the illustrated position, the liquid distribution system 2 is not fixed to the cycler. When fixation occurs, the shaft 62 is inserted through the opening 65 of the flexible U shape member 61 and retained to it by a retaining lip 63. When the liquid distribution system 2 is released from the cycler (downward movement) the bottom of the U shape member 61 is moved upwardly resulting in a movement of the clamping member 60 in the direction of the patient line 5. The patient line 5 will be kept closed as long as the shaft 62 is retained in the U shape member 61. To detach the liquid distribution system 2 completely from the cycler, the shaft 62 has to pass through a releasing slot 66.

Alternatively the patient line is closed by a special designed, so called "lip valve" which is normally closed. Due to a mechanical pin in the cycler the lip valve, as an integrated part of the membrane, will be open by simply pressed down with the pin coming from the cycler by mechanical movement.

Figure 14A:
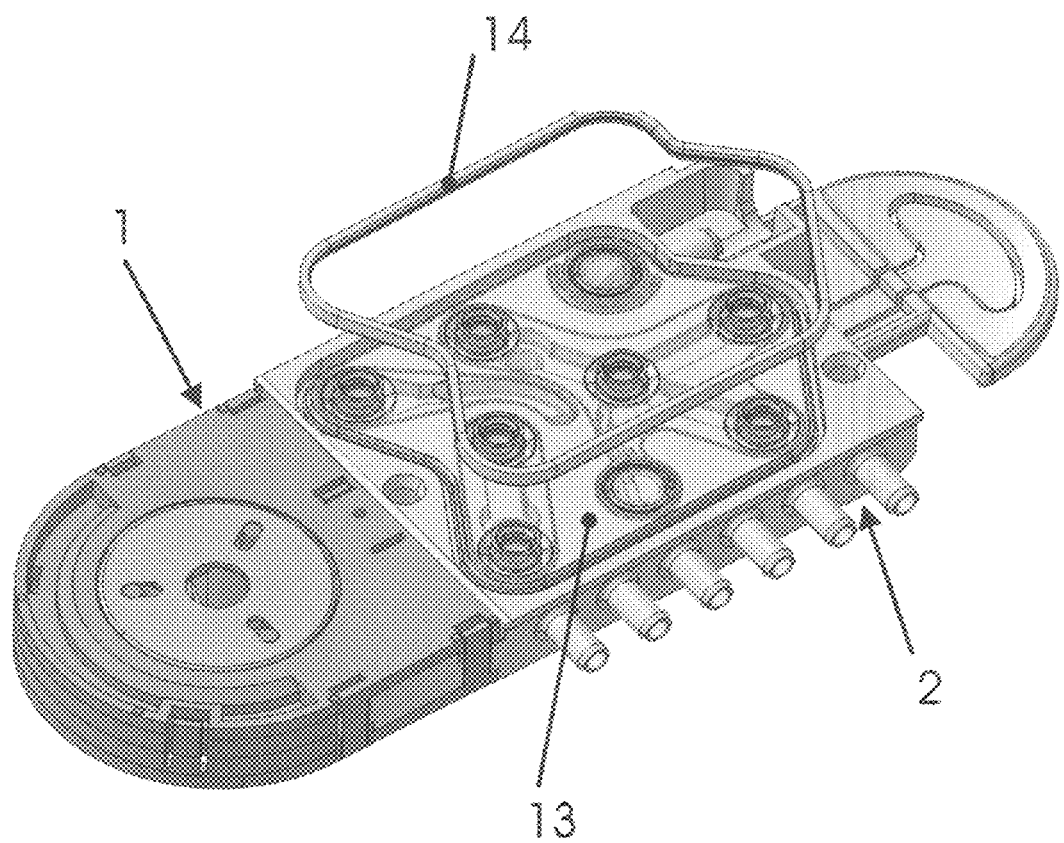

FIGS. 33 to 37 show another embodiment of the invention, similar to the embodiment of FIG. 14a, but which differs in that the membrane 13 is not fixed by a clipping frame but by a rigid plate 67 which covers the membrane 13 over its entire surface. The rigid plate has holes 70 adapted to receive the membrane actuator clips 39 and pins 68 adapted to be fixed on the cartridge 2. The membrane is provided with holes 69 which are designed to let the pins 68 pass through.

As can be seen on FIG. 37, the bottom side of the membrane 13 is provided with a flange 73 which is situated around the actuator clip 39. The cartridge 2 surface just below the flange 73 is provided with a groove 72. The groove 72 is adapted to receive and hold the flange 73 sufficiently enough to maintain a fluid tight connection between the membrane 13 and the cartridge 2.

This embodiment offers several advantages, in particular an improved distribution of the forces applied to the membrane 13.

In another embodiment of the invention (not illustrated) the system comprises one or several flow sensor(s) which is/are preferably situated close to the pump inlet and/or outlet.

The flow sensor may be of any type suitable for the intended purpose. For instance, but not exclusively, it may be of the mechanical (e.g. turbine flowmeter), mass (e.g. thermal flowmeter), electronic, magnetic or US type.

The invention claimed is:

1. A system for performing fluid administration on a patient comprising:
   a partial peristaltic pump (1),
   a liquid distribution system (2) that is a cartridge and that is separate from said pump and that is connected to said pump (1) in such a way that liquid can flow from the liquid distribution system (2) to the pump (1) and vice versa,
   liquid supply means (3) for supplying liquid to a patient (4) via said liquid distribution system (2) and said pump (1),
   a patient conduit (5) adapted for connecting said liquid distribution system (2) to a patient (4),
   wherein said liquid distribution system (2) comprises two distinct hub chambers (7,8) which are separated by a space, the first hub chamber (7) including at least one liquid supply port with dedicated valve means (9), one patient port with dedicated valve means (10) and one pump inlet (26), the second hub chamber (8) including at least one patient port (18) or warmer port (16) with dedicated valve means and one pump outlet (27), said system further comprising control means arranged to close said patient port (10) of the first hub chamber (7) when said liquid supply port (9) is open and vice versa and
   wherein all ports of the liquid distribution system that communicate with the pump are unidirectional such that liquid only flows in one direction.

2. System according to claim 1 wherein said second hub chamber (8) furthermore includes at least one drain port with dedicated valve means (11), said control means being also arranged to close said patient port (18) of the second hub chamber (8) when said drain port (11) is open and vice versa.

3. A system according to claim 1 wherein said liquid distribution system (2) only includes two hub chambers (7,8).

4. A system according to claim 1 furthermore comprising a warmer system (28), a cavity (17) including a warmer port (19) and a patient port (16), said patient port (18) of the second hub chamber (8) being connected to said warmer port (19) via said warmer system (28).

5. A system according to claim 4 wherein said warmer system (28) is a warmer in-line.

6. A system according to claim 5 wherein said warmer in-line comprises a warming plate contained therein, such warming plate being covered by a warming pouch.

7. A system according to claim 6 wherein said warming pouch is composed of a liquid channel which forces the liquid to be maintained within such warmer for a certain duration at a given flow rate.

8. A system according to claim 1 wherein said first hub chamber (7) includes several liquid supply ports with respective valve means (9).

9. A system according to claim 8 wherein said liquid supply ports (9) are connected to respective liquid supply means each having a different kind of liquid.

10. A system according to claim 1 wherein said peristaltic pump is unidirectional.

11. A system according to claim 1 wherein said pump (1) is composed of a tubing and rolling surface on which the tubing is compressed once the pump and liquid distribution system are inserted into a pumping device containing rollers.

12. A system according to claim 11 where said rollers (22) are of a conical shape in such a way as to be self inserted in the pump race, i.e. without any other mechanism.

13. A system according to claim 11 where said rollers are of a spherical shape.

14. A system according to claim 11 wherein said pump (1) comprises a flexible or partially flexible channel, a membrane covering said channel along an oblique plane, in order to allow a peristaltic movement induced by rollers or similar elements.

15. A system according to claim 14 comprising individual actuators or a cam adapted to induce a peristaltic movement.

16. A system according to claim 15 wherein said individual actuators are adapted to be actuated by fingers which are clipped to said membrane.

17. A system according to claim 1 wherein said pump (1) comprises a flexible or partially flexible channel and a series of movable finger elements successively situated above said channel, each finger element being movable along a direction which is substantially perpendicular to said channel, all finger elements being adapted to induce a peristaltic movement along said channel.

18. A system according to claim 17 wherein each finger element comprises a convex basis adapted to conform with the channel inner surface and a shaft adapted to be linked to an actuator.

19. A system according to claim 1 wherein said pump (1) and said liquid distribution system (2) are fixed together to form a single assembly.

20. A system according to claim 19 wherein said pump (1) is fixed to said liquid distribution system (2) by vibration attenuation means in order to minimize the vibration on the liquid distribution system (2) when the pump is operating.

21. A system according to claim 1 wherein all hub chambers, including said ports and ports, are made within one single part.

22. A system according to claim 21 wherein said single part is an injected part of plastic material.

23. A system according to claim 1 wherein each hub chamber (7,8) is closed with an upper wall made of a flexible membrane (13), said membrane including valve elements (39) situated above each of said port or port with valve means, said valve elements (39) being designed to close said port or port when the membrane (13) moves downwardly.

24. A system according to claim 23 wherein said membrane extends in such a way that it also covers said pump (1).

25. A system according to claim 23 wherein said membrane contains protruding elements designed for a liquid tight connection between said hub chambers.

26. A system according to claim 23 wherein each of said valve elements (39) is designed to be clipped to an actuator (34) arranged above said membrane (13).

27. A system according to claim 26 wherein each of said valve elements comprises a cavity designed to receive and hold the plunger of an actuator, said cavity having an height which substantially corresponds to at least the valve displacement.

28. A system according to claim 23 wherein said membrane (13) is press-fitted along its external border to the liquid distribution system, the membrane (13) being furthermore held by a frame (14).

29. A system according to claim 23 wherein said membrane (13) contains a portion (15) which is forming part of a pressure sensor.

30. A system according to claim 29 wherein the active area of said pressure sensor is designed to be more flexible than the remaining area.

31. A system according to claim 29 wherein said pressure sensor has the shape of a disc of which the periphery is gripped, said disc furthermore comprising an annular ply.

32. A system according to claim 29 wherein said pressure sensor is situated on the patient line, independently from said hub chambers.

33. A system according to claim 29 furthermore comprising a second pressure sensor, said second pressure sensor being in connection with the first hub chamber.

34. A pressure sensor for a system for performing fluid administration on a patient as defined in claim 29.

35. A system according to claim 23 comprising a molded frame adapted to cover the space between said hub chambers, each space above said hub chambers being covered by a flexible membrane.

36. A system according to claim 35 wherein said molded frame is fixed to said liquid distribution system by ultrasound, laser welding, gluing or thermal bonding.

37. A system according to claim 35 wherein said molded frame is at least partially made of silicone or polyurethane.

38. A system according to claim 35 wherein said frame, membrane and liquid distribution system are obtained by overmolding technique.

39. A system according to claim 23 using a double layer membrane adapted to prevents spallation or particle release into the fluid during use.

40. A system according to claim 23 furthermore comprising a rigid plate (67) which covers and holds the membrane (13), said rigid plate (67) comprising holes (70) adapted to let moving elements passing through.

41. A system according to claim 40 wherein said rigid plate (67) includes pins (68) situated on the membrane side, said pins (68) being adapted to be fixed on the liquid distribution system (2).

42. A system according to claim 1 wherein each hub chamber (7,8) is closed with an upper wall made of a flexible membrane (13), said membrane including clipping means adapted to clip elements.

43. A system according to claim 42 wherein said membrane is molded.

44. A system according to claim 43 wherein said membrane is made out of any of the following materials: silicone or polyurethane.

45. A system according to claim 44 wherein said membrane includes liquid tight joints.

46. A system according to claim 1 wherein said liquid distribution system includes liquid tight joints arranged in such a manner that they allow a liquid tight connection between said liquid distribution system and a membrane situated on it.

47. A system according to claim 1 wherein said liquid distribution system includes an air sensor situated on the patient conduit side.

48. A system according to claim 1 comprising a cartridge loading mechanism which allows a tight connection between the membrane and the valves and the liquid distribution system.

49. A system according to claim 1 comprising flow blocking means adapted to block the flow towards or from the liquid distribution system when this latter one is released out of the system.

50. A system according to claim 49 wherein said blocking means is a mechanical clamp situated on the patient line.

51. A system according to claim 49 wherein said blocking means is a lip valve situated on the patient line, the system furthermore comprises a movable pin adapted to open said lip valve when the liquid distribution system is released out of the system.

52. A system according to claim 1 furthermore comprising a window for detecting correct positioning of the tube.

53. A liquid distribution system (2) for a system performing fluid administration on a patient as defined in claim 1.

54. Method of use of the system as defined in claim 1 wherein said patient port (10) is closed when said liquid supply port (9) is open and vice versa.

55. Method according to claim 54 wherein the pressure is always maintained positive with respect to the drain.

56. Method according to claim 54 wherein said liquid is always pumped in the same direction.

57. Method according to claim 54 consisting of sensing the liquid pressure entering and exiting the liquid distribution system and, if necessary, correct the pump flow rate in accordance with the pressure difference.

58. Method according to claim 54 consisting in regulating the pump flow rate according to a known predetermined alteration of the flow rate by aging of the tubing.

59. Method according to claim 54 wherein the drain phase is a function of the drain speed, said drain phase being ended when the speed is reaching a certain value based on the patient peritoneal cavity pressure measurement.

60. Method according to claim 54 wherein the peritoneal volume filled during a cycle is a function of the intra-peritoneal pressure.

61. Method according to claim 60 wherein the peritoneal cavity is partially emptied as soon as the pressure has reached a predefined threshold.

62. Method according to claim 54 consisting in the use of a low Natrium concentration liquid for the last exchange cycle to improve ultra-filtration.

63. Use of a system as defined in claim 1 for peritoneal dialysis comprising:
   selecting a liquid,
   supplying the liquid to a patient via use of the system for peritoneal dialysis.

64. A disposable cassette for use in performing fluid administration on a patient comprising:
   a partial peristaltic pump (1),
   a liquid distribution system (2) in a substantially rectangular-shaped member that is separate from said pump and that is abutted to a side of said pump (1) in such a way that liquid can flow from the liquid distribution system (2) to the pump (1) and vice versa,
   liquid supply means (3) for supplying liquid to a patient (4) via said liquid distribution system (2) and said pump (1),
   a patient conduit (5) adapted for connecting said liquid distribution system (2) to a patient (4),
   wherein said liquid distribution system (2) comprises a first hub chamber and a distinct second hub chamber (7,8) which are separated by a space,
   the first hub chamber (7) including at least one liquid supply port with dedicated valve means (9), one patient port with dedicated valve means (10) and one pump inlet (26),
   the second hub chamber (8) including at least one patient port (18) or warmer port (16) with dedicated valve means and one pump outlet (27),
   said system further comprising control means arranged to close said patient port (10) of the first hub chamber (7) when said liquid supply port (9) is open and vice versa, and
   wherein all ports of the liquid distribution system that communicate with the pump are unidirectional ports.

* * * * *